(12) United States Patent
Sebti

(10) Patent No.: US 7,951,924 B2
(45) Date of Patent: May 31, 2011

(54) RHOB VARIANTS AND METHODS OF USE

(75) Inventor: Said M. Sebti, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 11/274,368

(22) Filed: Nov. 14, 2005

(65) Prior Publication Data

US 2006/0105374 A1 May 18, 2006

Related U.S. Application Data

(60) Provisional application No. 60/627,270, filed on Nov. 12, 2004.

(51) Int. Cl.
C07H 21/02 (2006.01)
(52) U.S. Cl. .................... 536/23.1; 536/23.5
(58) Field of Classification Search .............. None
See application file for complete search history.

(56) References Cited

U.S. PATENT DOCUMENTS

| | | | | |
|---|---|---|---|---|
| 7,144,711 | B2 * | 12/2006 | Cismowski et al. | ............ 435/29 |
| 2002/0034725 | A1 | 3/2002 | McKenna et al. | |
| 2003/0018003 | A1 | 1/2003 | Sebti | |
| 2004/0171547 | A1 | 9/2004 | Sebti | |
| 2006/0137042 | A1 * | 6/2006 | Plesch et al. | ............ 800/288 |

FOREIGN PATENT DOCUMENTS

WO     WO 01/97828 A2     12/2001

OTHER PUBLICATIONS

Adamson et al., J Biol Chem, 1992, 267:20033-20038.*
Adamson, P. et al. "Post-translational modifications of p21$^{rho}$ proteins" *J Biol Chem*, 1992, 267:20033-20038.
Adjei, A.A. "Ras signaling pathway proteins as therapeutic targets" *Curr Pharm Design*, 2001, 7:1581-1594.
Adnane, J. et al. "Suppression of Rho B expression in invasive carcinoma from head and neck cancer patients" *Clin Cancer Res*, 2002, 8:2225-2232.
Adnane, J. et al. "RhoB, not RhoA, represses the transcription of the transforming growth factor β type II receptor by a mechanism involving activator protein 1" *J Biol Chem*, 2002, 277:8500-8507.
Alimandi, M. et al. "Cooperative signaling of ErbB3 and ErbB2 in neoplastic transformation and human mammary carcinomas" *Oncogene*, 1995, 10:1813-1821.
Arboleda, M.J. et al. "Overexpression of AKT2/protein kinase Bβ leads to up-regulation of β1 integrins, increased invasion, and metastasis of human breast and ovarian cancer cells" *Cancer Res*, 2003, 63:196-206.
Armstrong, S.A. et al. "CAAX geranylgeranyl transferase transfers farnesyl as efficiently as geranylgeranyl to RhoB" *J Biol Chem*, 1995, 270:7864-7868.
Barbacid, M. "ras Genes" *Annu. Rev. Biochem.*, 1987, 56:779-827.
Baron, R. et al. "RhoB prenylation is driven by the three carboxylterminal amino acids of the protein: Evidenced in vivo by an anti-farnesyl cysteine antibody" *Proc Natl Acad Sci USA*, 2000, 97:11626-11631.
Bos, J.L. "*ras* oncogenes in human cancer: A review" *Cancer Res.*, 1989, 49:4682-4689.
Buday, L. and Downward, J. "Epidermal growth factor regulates p21$^{ras}$ through the formation of a complex of receptor, Grb2 adaptor protein, and Sos nucleotide exchange factor" *Cell*, 1993, 73:611-620.
Campbell, S.L. et al. "Increasing complexity of Ras signaling" *Oncogene*, 1998, 17:1395-1413.
Caponigro, F. "Farnesyl transferase inhibitors: a major breakthrough in anticancer therapy?" *Anti-Cancer Drugs*, 2002, 13:891-897.
Chang, F. et al. "Signal transduction mediated by the Ras/Raf/MEK/ERK pathway from cytokine receptors to transcription factors: potential targeting for therapeutic intervention" *Leukemia*, 2003, 17:1263-1293.
Chardin, P. et al. "Coding sequence of human *rho* cDNAs clone 6 and clone 9" *Nucleic Acids Res.* 1988, 16: 2717.
Chen, Z. et al. "Both farnesylated and geranylgeranylated RhoB inhibit malignant transformation and suppress human tumor growth in nude mice" *J Biol Chem*, 2000, 275(24):17974-17978.
Chen, Z. et al. "Farnesylated and geranylgeranylated RhoB suppress the transformation of PANC-1 human pancreatic cancer cells" Proceedings of the 91$^{st}$ Annual Meeting of the American Association of Cancer Research, vol. 14, p. 220, abstract No. 1402, 2000.
Clark, E.A. et al. "Genomic analysis of metastasis reveals an essential role for RhoC" *Nature*, 2000, 406:532-535.
Cox, A.D. et al. "Farnesyltransferase inhibitors and cancer treatment: targeting simply Ras?" *Biochim. Biophys. Acta.*, 1997, 1333:F51-F71.
Davies, M.A. et al. "Adenoviral-mediated expression of MMAC/PTEN inhibits proliferation and metastasis of human prostate cancer cells" *Clin Cancer Res*, 2002, 8:1904-1914.
Downward, J. "Targeting Ras signaling pathways in cancer therapy" *Nat Rev Cancer*, 2003, 3:11-22.
Du, W. et al. "Cell growth inhibition by farnesyltransferase inhibitors in mediated by gain of geranylgeranylated RhoB" *Mol Cell Biol*, 1999, 19(3):1831-1840.
Du, W. and Prendergast, G.C. "Geranylgeranylated RhoB mediates suppression of human tumor cell growth by farnesyltransferase inhibitors" *Cancer Res*, 1999, 59:5492-5496.
End, D.W. et al. "Characterization of the antitumor effects of the selective farnesyl protein transferase inhibitor R115777 in vivo and in vitro" *Cancer Res.*, 2001, 61:131-137.
Forget, M.A. et al. "The expression of Rho proteins decreases with human brain tumor progression: potential tumor markers" *Clin Exp Metastasis*, 2002, 19(1):9-15.

(Continued)

*Primary Examiner* — Misook Yu
*Assistant Examiner* — Mark Halvorson
(74) *Attorney, Agent, or Firm* — Saliwanchik, Lloyd & Eisenschenk

(57) ABSTRACT

In one aspect, the present invention concerns RhoB variant polypeptides and isolated degenerate polynucleotides encoding the RhoB variant polypeptides. In another aspect, the present invention concerns nucleic acid constructs containing a polynucleotide encoding a RhoB variant polypeptide, and host cells genetically modified to express such polynucleotides. In another aspect, the present invention provides a method of inhibiting the growth of, and inducing apoptosis in, cancerous cells by contacting the cells with an effective amount of a RhoB variant.

24 Claims, 11 Drawing Sheets

OTHER PUBLICATIONS

Fritz, G. et al. "The Ras-related small GTP-binding protein RhoB is immediate-early inducible by DNA damaging treatments" *J Biol Chem*, 1995, 270(42):25172-25177.

Fritz, G. and Kaina, B. "*rhoB* encoding a UV-inducible Ras-related small GTP-binding protein is regulated by GTPases of the Rho family and independent of JNK, ERK, and p38 MAP kinase" *J Biol Chem*, 1997, 272(49):30637-30644.

Fritz, G. and Kaina, B. "Ras-related GTPase RhoB represses NF-κB signaling" *J Biol Chem*, 2001, 276:3115-3122.

Fukata, M. et al. "Roles of Rho-family GTPases in cell polarisation and directional migration" *Curr Opin Cell Biol*, 2003, 15:590-597.

GENBANK accession No. X06820, "*H. sapiens* rhoB gene mRNA" Oct. 24, 1996.

GENBANK accession No. CAA29968, "rhoB [*Homo sapiens*]" Oct. 24, 1996.

Gibbs, J.B. et al. "The potential of farnesyltransferase inhibitors as cancer chemotherapeutics" *Annu. Rev. Pharmacol. Toxicol.*, 1997, 37:143-166.

Gura, T. "Systems for identifying new drugs are often faulty" *Science*, 1997, 278:1041-1042.

Hall, A. "Rho GTPases and the actin cytoskeleton" *Science*, 1998, 279(5350):509-514.

Hunter, T. "Oncoprotein networks" *Cell*, 1997, 88:333-346.

Jahner, D. and Hunter, T. "The *ras*-related gene *rho B* is an immediate-early gene inducible by v-Fps, epidermal growth factor, and platelet-derived growth factor in rat fibroblasts" *Mol Cell Biol*, 1991, 11(7):3682-3690.

Jiang, K. et al. "Regulation of Akt-dependent cell survival by Syk and Rac" *Blood*, 2003, 101:236-244.

Jiang, K. et al. "Akt mediates Ras downregulation of RhoB, a suppressor of transformation, invasion, and metastasis" *Mol Cell Biol*, 2004, 24:5565-5576.

Jiang, K. et al. "EGFR, ErbB2 and Ras but not Src suppress RhoB expression while ectopic expression of RhoB antagonizes oncogene-mediated transformation" *Oncogene*, 2004, 23:1136-1145.

Kerbel, R.S. "Human tumor xenografts as predictive preclinical models for anticancer drug activity in humans" *Cancer Biol. & Ther.*, 2003, 2(4 Supp. 1):S134-S139.

Khosravi-Far, R. and Der, C.J. "The Ras signal transduction pathway" *Cancer Metastasis Rev*, 1994, 13:67-89.

Khosravi-Far, R. et al. "Activation of Rac1, RhoA, and mitogen-activated protein kinases is required for Ras transformation" *Mol Cell Biol*, 1995, 15(11):6443-6453.

Kim, D. et al. "Akt/PKB promotes cancer cell invasion via increased motility and metalloproteinase production" *Faseb J*, 2001, 15:1953-1962.

Kubiatowski, T. et al. "Association of increased phosphatidylinositol 3-kinase signaling with increased invasiveness and gelatinase activity in malignant gliomas" *J Neurosurg*, 2001, 95:480-488.

Lebowitz, P.F. et al. "Evidence that farnesyltransferase inhibitors suppress Ras transformation by interfering with Rho activity" *Mol Cell Biol*, 1995, 15(12):6613-6622.

Lebowitz et al. "Farnesyltransferase inhibitors alter the prenylations and growth-stimulating function of RhoB" *JBC*, 1997, 272(25):15591-15594.

Lebowitz, P.F. and Prendergast, G.C. "Non-Ras targets of farnesyltransferase inhibitors: focus on Rho" *Oncogene*, 1998, 17:1439-1445.

Lebowitz, P.F. et al. "Prenylation of RhoB is required for its cell transforming function but not its ability to activate serum response element-dependent transcription" *J Biol Chem*, 1997, 272:16093-16095.

Liu and Jessell "A role for rhoB in the delamination of neural crest cells from the dorsal beural tube" *Development*, 1998, 125:5055-5067.

Liu, A. et al. "RhoB alteration is necessary for apoptotic and antineoplastic responses to farnesyltransferase inhibitors" *Mol Cell Biol*, 2000, 20(16):6105-6113.

Liu, A. et al. "RhoB is required to mediate apoptosis in neoplastically transformed cells after DNA damage" *Proc Natl Acad Sci USA*, 2001, 98(11):6192-6197.

Liu, A-X. et al. "RhoB is dispensable for mouse development, but it modifies susceptibility to tumor formation as well as cell adhesion and growth factor signaling in transformed cells" *Mol Cell Biol*, 2001, 21:6906-6912.

Luetteke, N.C. et al. "The mouse *waved-2* phenotype results from a point mutation in the EGF receptor tyrosine kinase" *Genes Dev*, 1994, 8:399-413.

Marshall "Second child in French trial is found to have aleukemia" *Science*, 2003, 299:320.

Mazieres, J. et al. "Loss of RhoB expression in human lung cancer progression" *Clin Cancer Res*, 2004, 10:2742-2750.

McCormick, F. "How receptors turn Ras on" *Nature*, 1993, 363:15-16.

Mellor, H. et al. "PRK1 is targeted to endosomes by the small GTPase, RhoB" *J. Biol. Chem.*, 1998, 273:4811-4814.

Meng and El-Deiry "Tumor suppressor genes as targets for cancer gene therapy" *Gene Therapy of Cancer*, Chapter 1, pp. 3-18, 1999.

Nakamura, T. et al. "Cloning of the RhoB gene from the mouse genome and characterization of its promoter region" *Biochem. Biophys. Res. Commun.*, 1996, 226(3):688-694.

Nobes, C.D. and Hall, A. "Rho, Rac, and Cdc42 GTPases regulate the assembly of multimolecular focal complexes associated with actin stress fibers, lamellipodia, and filopodia" *Cell*, 1995, 81:53-62.

Olson, M.F. et al. "An essential role for Rho, Rac, and Cdc42 GTPases in cell cycle progression through $G_1$" *Science*, 1995, 269:1270-1272.

Park, B-K. et al. "Akt1 induces extracellular matrix invasion and matrix metalloproteinase-2 activity in mouse mammary epithelial cells" *Cancer Res*, 2001, 61:7647-7653.

Prendergast, G.C. and Rane, N. "Farnesyltransferase inhibitors: mechanism and applications" *Expert Opin. Investig. Drugs*, 2001, 10:2105-2116.

Pruitt, K. and Der, C.J. "Ras and Rho regulation of the cell cycle and oncogenesis" *Cancer Lett.*, 2001, 171(1):1-10.

Qiu, R.G. et al. "An essential role for Rac in Ras transformation" *Nature*, 1995, 374:457-459.

Ouilliam, L.A. et al. "Identification of residues critical for Ras(17N) growth-inhibitory phenotype and for Ras interaction with guanine nucleotide exchange factors" *Mol Cell Biol*, 1994, 14(2):1113-1121.

Reuter, C.W. et al. "Targeting the Ras signaling pathway: a rational, mechanism-based treatment for hematologic malignancies?" *Blood*, 2000, 96:1655-1669.

Robson, T. and Hirst, D. "Transcriptional targeting in cancer gene therapy" *J. Biomed. Biotech.*, 2003, 2:110-137.

Sebti, S.M. and Hamilton, A.D. "Inhibition of Ras prenylation: A novel approach to cancer chemotherapy" 1997, 74:103-114.

Shi, B. et al. "The farnesyl protein transferase inhibitor SCH66336 synergizes with taxanes in vitro and enhances their antitumor activity in vivo" *Cancer. Chemother. Pharmacol.*, 2000, 46:387-393.

Stewart, A.L. et al. "PI3K blockade by Ad-PTEN inhibits invasion and induces apoptosis in radial growth phase and metastatic melanoma cells" *Mol Med*, 2002, 8(8):451-461.

Sun, J. et al. "Antitumor efficacy of a novel class of non-thiol-containing peptidomimetic inhibitors of farnesyltransferase and geranylgeranyltransferase I: Combination therapy with the cytotoxic agents cisplatin, taxol, and gemcitabine" *Cancer Res.*, 1999, 59:4919-4926.

Symons, M. and Settleman, J. "Rho family GTPases: more than simple switches" *Trends Cell Biol*, 2000, 10(10):415-419.

Symons, M. and Rusk, N. "Control of vesicular trafficking by Rho GtPases" *Curr Biol*, 2003, 13:R409-418.

Torchilin and Lukyanov "Peptide and protein drug delivery to and into tumors: challenges and solutions" *Drug Discover Today*, 2003, 8:259-265.

Turkson, J. et al. "Requirement for Ras/Rac1-mediated p38 and c-Jun N-terminal kinase signaling in Stat3 transcriptional activity induced by the Src oncoprotein" *Mol Cell Biol*, 1999, 19(11):7519-7528.

Van Aelst, L. and D'Souza-Schorey, C. "Rho GTPases and signaling networks" *Genes Dev*, 1997, 11(18):2295-2322.

Verma and Somia "Gene therapy-promises, problems and prospects" *Nature*, 1997, 389:239-242.

Vlahos, C.J. et al. "A specific inhibitor of phosphatidylinositol 3-kinase, 2-(4-morpholinyl)-8-phenyl-4H-1-benzopyran-4-one (LY294002)" *J Biol Chem*, 1994, 269(7):5241-5248.

Voskoglou-Nomikos, T. et al. "Clinical predictive value of the in vitro cell line, human xenograft, and mouse allograft preclinical cancer models" *Clin. Cancer Res.*, 2003, 9:4227-4239.

Wang, D-A and Sebti, S.M. "Palmitoylated cysteine 192 is required for RhoB tumor suppressive and apoptotic activities" Presentation at the American Association for Cancer Research, Anaheim, CA, Apr. 16-20, 2005, abstract.

Wang, D-A. and Sebti, S.M. "Palmitoylated cysteine 192 is required for RhoB tumor-suppressive and apoptotic activities" *J. Biol. Chem.*, 2005, 280:19243-19249.

Welsh, C.F. "Rho GTPases as key transducers of proliferative signals in $G_1$ cell cycle regulation" *Breast Cancer Res Treat*, 2004, 84:33-42.

Yano, H. et al. "Biochemical and pharmacological studies with KT7692 and LY294002 on the role of phosphatidylinositol 3-kinase in FcϵRI-mediated signal transduction" *Biochem J*, 1995, 312(Pt 1):145-150.

Zhang, F.L. and Casey, P.J. "Protein prenylation: Molecular mechanisms and functional consequences" *Annu. Rev. Biochem.*, 1996, 65:241-269.

Zohn, I.M. et al. "Rho family proteins and Ras transformation: the RHOad less traveled gets congested" *Oncogene*, 1998, 17:1415-1438.

Zeng, P-Y. et al. "Role for RhoB and PRK in the suppression of epithelial cell transformation by farnesyltransferase inhibitors" *Oncogene*, 2003, 22:1124-1134.

* cited by examiner

RhoA  MAAIRKKLV I 10 VGDGACGKTC 20 LLIVFSKDQF 30 PEVYVPTVFE 40
RhoB  MAAIRKKLVV 10 VGDGACGKTC 20 LLIVFSKDEF 30 PEVYVPTVFE 40
                *                                *

RhoA  NYVADIEVDG 50 KQVELALWDT 60 AGQEDYDRLR 70 PLSYPDTDVI 80
RhoB  NYVADIEVDG 50 KQVELALWDT 60 AGQEDYDRLR 70 PLSYPDTDVI 80

RhoA LMCFSIDSPD 90 SLENIPEKWT 100 PEVKHFCPNV 110 PIILVGNKKD 120
RhoB LMCFSVDSPD 90 SLENIPEKWV 100 PEVKHFCPNV 110 PIILVANKKD 120
          *                  *                        *
RhoA LRNDEHTRRE 130 LAKMKQEPVK 140 PEEGRDMANR 150 IGA FGYMECS 160
RhoB LRSDEHVRTE 130 LARMKQEPVR 140 TDDGRAMAVR 150 IQAYDY LECS 160
       *  *  *        *           ***  *  *      *  **  *
RhoA AKTKDGVREV 170 FEMATRAALQ 180 ARRGKKK---  SGC 190 LVL
RhoB AKTKE GVREV 170 FETATRA ALQ 180 KRYGSQNGCINCC 193 KVL
         *              *           *  *  *******     *

FIG. 1A

RHOB VARIANTS AND METHODS OF USE

CROSS-REFERENCE TO RELATED APPLICATION

The present application claims benefit of U.S. Provisional Application Ser. No. 60/627,270, filed Nov. 12, 2004, which is hereby incorporated by reference herein in its entirety, including any figures, tables, nucleic acid sequences, amino acid sequences, and drawings.

GOVERNMENT SUPPORT

The subject matter of this application has been supported by a research grant from the National Institutes of Health under grant number NCDDG U19 CA67771. Accordingly, the government may have certain rights in this invention.

BACKGROUND OF THE INVENTION

Rho proteins are GTP/GDP binding GTPases that belong to the Ras superfamily and are intimately involved in diverse cellular processes and diseases (Symons, M. and Rusk, N. *Curr Biol,* 2003, 13:R409-418). For example, Rho proteins are pivotal in the regulation of actin cytoskeleton processes such as lamillopodia, fiber and membrane ruffle formation (Fukata, M. et al. *Curr Opin Cell Biol,* 2003, 15:590-597; Nobes, C. D. and Hall, A. *Cell,* 1995, 81:53-62). Rho proteins also regulate signal transduction proteins such as Erks, p38 and SAPK, that are involved in the mitogen- and stress-activated kinase pathways (Chang, F. et al. *Leukemia,* 2003, 17:1263-1293). Most important is the involvement of Rho GTPases as mediators of proliferation and malignant transformation. For example, RhoA and Rac1 are critical for the G1/S cell division cycle traverse (Welsh, C. F. *Breast Cancer Res Treat,* 2004, 84:33-42), and mediate oncogenic Ras malignant transformation (Welsh, C. F. *Breast Cancer Res Treat,* 2004, 84:33-42; Downward, J. *Nat Rev Cancer,* 2003, 3:11-22). In cellular and animal models Rho proteins such as RhoA, Rac1, cdc42 and RhoC have been implicated in invasion and metastasis, and RhoC has been shown to contribute to metastasis in clinical settings (Welsh, C. F. *Breast Cancer Res Treat,* 2004, 84:33-42; Downward, J. *Nat Rev Cancer,* 2003, 3:11-22; Clark, E. A. et al. *Nature,* 2000, 406:532-535).

While most Rho proteins are involved in promoting oncogenesis, invasion and/or metastasis, mounting evidence points to a tumor suppressive role for RhoB. First, in cultured cells, RhoB inhibits oncogenic signaling (Chen, Z. et al. *J Biol Chem,* 2000, 275:17974-17978; Fritz, G. and Kaina, B. *J Biol Chem,* 2001, 276:3115-3122), and anchorage-dependent and -independent tumor cell growth (Chen, Z. et al. *J Biol Chem,* 2000, 275:17974-17978) and induces apoptosis (Chen, Z. et al. *J Biol Chem,* 2000, 275:17974-17978; Liu, A. et al. *Mol Cell Biol,* 2000, 20:6105-6113). Second, ectopic expression of RhoB suppresses the growth of human cancer cells in nude mice (Chen, Z. et al. *J Biol Chem,* 2000, 275: 17974-17978; Jiang, K. et al. *Mol Cell Biol,* 2004, 24:5565-5576). Third, RhoB knockout mice are more sensitive to chemically-induced tumors (Liu, A. X. et al. *Mol Cell Biol,* 2001, 21:6906-6912) and RhoB (−/−) cells are resistant to apoptosis induced by radiation and cytotoxic agents (Liu, A. et al. *Proc Natl Acad Sci USA,* 2001, 98:6192-6197). Fourth, ectopic expression of RhoB suppresses EGFR, ErbB2, Ras, PI3K and Akt induced tumor survival, proliferation, invasion and metastasis (Jiang, K. et al. *Mol Cell Biol,* 2004, 24:5565-5576; Jiang, K. et al. *Oncogene,* 2004, 23:1136-1145). Fifth, many oncogenes such as EGFR, Ras and Akt suppress the expression of RhoB (Jiang, K. et al. *Mol Cell Biol,* 2004, 24:5565-5576; Jiang, K. et al. *Oncogene,* 2004, 23:1136-1145). Finally, in patients with head and neck, lung and brain cancers, RhoB protein levels are drastically decreased as the tumors become more aggressive and highly invasive (Adnane, J. et al. *Clin Cancer Res,* 2002, 8:2225-2232; Mazieres, J. et al. *Clin Cancer Res,* 2004, 10:2742-2750; Forget, M. A. et al. *Clin Exp Metastasis,* 2002, 19:9-15). The above studies suggest that RhoB plays a critical role in suppressing malignant transformation by blocking oncogenic and tumor survival pathways, and that oncogenes such as Ras and EGFR suppress RhoB expression as a step towards malignant transformation.

The fact that RhoA and RhoB have opposing effects on malignant transformation is intriguing considering that RhoA and RhoB share 86% amino acid identity. Presently, it is not understood why RhoA promotes, whereas RhoB suppresses, malignant transformation. The present inventor has carried out site-directed mutagenesis studies with the goal of identifying those amino acids in RhoB that are critical to its tumor suppressive activity.

BRIEF SUMMARY OF THE INVENTION

The fact that RhoA and RhoB have opposing effects on malignant transformation is intriguing considering that RhoA and RhoB share 86% amino acid identity. RhoA promotes, whereas RhoB suppresses, malignant transformation. The present inventor has carried out site-directed mutagenesis studies with the goal of identifying those amino acids in RhoB that are critical to its tumor suppressive activity. These studies have resulted in the generation of RhoB variants that retain RhoB function.

The present invention pertains to methods of reducing the growth of a cancerous cell by contacting the cell with an effective amount of a RhoB variant.

The present invention concerns the use of variants of the RhoB protein to inhibit cancer cell growth, metastasis, invasion, migration, malignant cell transformation, and/or to modulate oncogenic signaling. According to the methods of the present invention, one or more RhoB variant polypeptides are introduced directly, or indirectly via a nucleic acid sequence encoding the RhoB variant polypeptide, into a malignantly transformed cell or a cancerous cell, wherein the RhoB variant polypeptide suppresses tumor growth and promotes apoptosis ("programmed cell death"). Therefore, the desirable goals of promoting apoptosis of cancerous cells and suppressing tumor growth within a patient are accomplished through administration of a RhoB variant polypeptide or encoding polynucleotide, which can be administered as a simple compound or in a pharmaceutical composition with a pharmaceutically acceptable carrier. RhoB variants can be used alone or in combination with additional anti-cancer agents, such as cytotoxic agents (e.g., 5-flurouracil, TAXOL) and/or anti-signaling agents (e.g., the PI3K inhibitor LY).

In another aspect, the present invention concerns isolated RhoB variant polypeptides and isolated degenerate polynucleotides encoding the RhoB variant polypeptides. In another aspect, the present invention concerns nucleic acid constructs containing a polynucleotide encoding a RhoB variant polypeptide. In one embodiment, the RhoB variant polypeptide has both a palmitoylated cysteine 192 and prenylated cysteine 193, or a conservative substitution of one or both of these amino acids.

Amino acids 29, 100, 116, 123, 129, 140-143, 141, 146, 152, 154, 155, 173, 181, 183-187, 189, 190, 191, 192 and 193 in RhoB were mutated to the corresponding RhoA residues to determine those critical for RhoB tumor suppressive activity. Out of all the mutants made, only cysteine 192 (one of two palmitoylation sites) and cysteine 193 (the prenylation site) point mutations abolish RhoB functions. In contrast, mutation of the other palmitoylation site, cysteine 189, did not affect RhoB functions. Moving cysteine 192 to position 190 did not affect RhoB function either. Mutation of cysteine 192 to glycine, alanine or serine blocks the ability of RhoB to suppress TGFβ type II receptor, p21waf and AP-1 promoter transcriptional activities. Furthermore, mutations of cysteines 192 and 193, but not 189, mislocalize RhoB and prevent RhoB from inhibiting anchorage-dependent and -independent tumor growth and colony formation as well as from inducing apoptosis. These results demonstrate that the presence of neither cysteine 193 nor cysteine 192 alone is sufficient and that both palmitoylated cysteine 192 and prenylated cysteine 193, but not palmitoylated cysteine 189, are required for RhoB tumor suppressive and pro-apoptotic activities.

BRIEF DESCRIPTION OF THE DRAWINGS

FIGS. 1A-1E show that the ability of RhoB to suppress the promoter activity of p21 waf, AP1 and TGFβR requires cysteine 192. F*igure* 1A shows the sequence homology of human RhoA (SEQ ID NO:53) and RhoB (SEQ ID NO:54) (* designates residues that are different). FIG. 1B shows the expression levels of RhoB, RhoA and mutant constructs as measured by HA antibody Western immunoblotting as described under Materials and Methods. In FIGS. 1C, 1D, and 1E, Panc-1 cells were cotransfected with luciferase under the control of TGF βII receptor, P21 waf and AP1 promoters, respectively. In each experiment the luciferase activity was normalized for transfection efficiency against β-galactosidase activity and expressed as relative luciferase activity. Bars represent standard deviation. The data are representative of three independent experiments. * designates p values with respect to differences with RhoB (F*igure* 1C, all p values <0.005; FIG. 1D, p<0.01; FIG. 1E p<0.01).

In FIG. 2A, HEK293 cells were transfected with RhoB, RhoB mutants (C192G, C192S, C192A, CC(189,192)SS, C193S, C189S), RhoA, or vector and labeled with [$^{14}$C] palmitic acid as described under Materials and Methods. Aliquots of the supernatant of total cell lysates were analyzed for expression levels by Western blot with anti-HA antibody and the rest of the supernatants immunoprecipitated with anti-HA agarose and were analyzed on 12.5% SDS-PAGE gels for autoradiography. In FIG. 2B, HEK293 cells were transfected with above constructs and stained with anti-HA and fluorescein isothiocyanate-conjugated anti-mouse IgG secondary antibody. Cells were visualized using a fluorescence microscope. In FIG. 2C, in vitro translation/prenylation of RhoA, RhoB, H-Ras, C192S, RhoB and C193S RhoB mutants was performed as described under Materials and Methods.

FIG. 3A shows MTT assay. Cells were plated in 96-well plates and transfected with the indicated constructs for 30 hours. After replacing transfection medium with fresh medium, cells were incubated for two days then stained with MTT. * designates p<0.005 with respect to differences with RhoB. FIG. 3B shows colony formation. Panc-1 cells were transfected with constructs RhoA, RhoB, C192G, C192S, C192A, CC(189,192)SS, C193S, C189S, or vector and after two days were counted and seeded into six well plates. Colonies were counted 3 weeks later. FIG. 3C shows Soft agar assay. Panc-1 cells were transfected as in FIG. 3B, then cells were seeded into 0.3% agar over a bottom 0.6% agar layer in 10% FBS/DMEM. Colonies stained and counted four weeks later as described under Materials and Methods. The difference between RhoB and vector, RhoA, C192S and C193S was statistically significant with p<0.05 for both FIGS. 3B and 3C.

FIG. 4A shows TUNEL assay. PC-3 cells were transfected with RhoA, RhoB, RhoA/RhoB chimera, C192S, C193S, C189S and vector, and spun onto slides to monitor apoptosis determination by TUNEL reaction. FIG. 4B shows the percentage of TUNEL-positive cells. Bars represent standard deviation. The data are representative of three independent experiments. * designates p<0.005 with respect to differences with RhoB.

BRIEF DESCRIPTION OF THE SEQUENCES

Figure 1B:
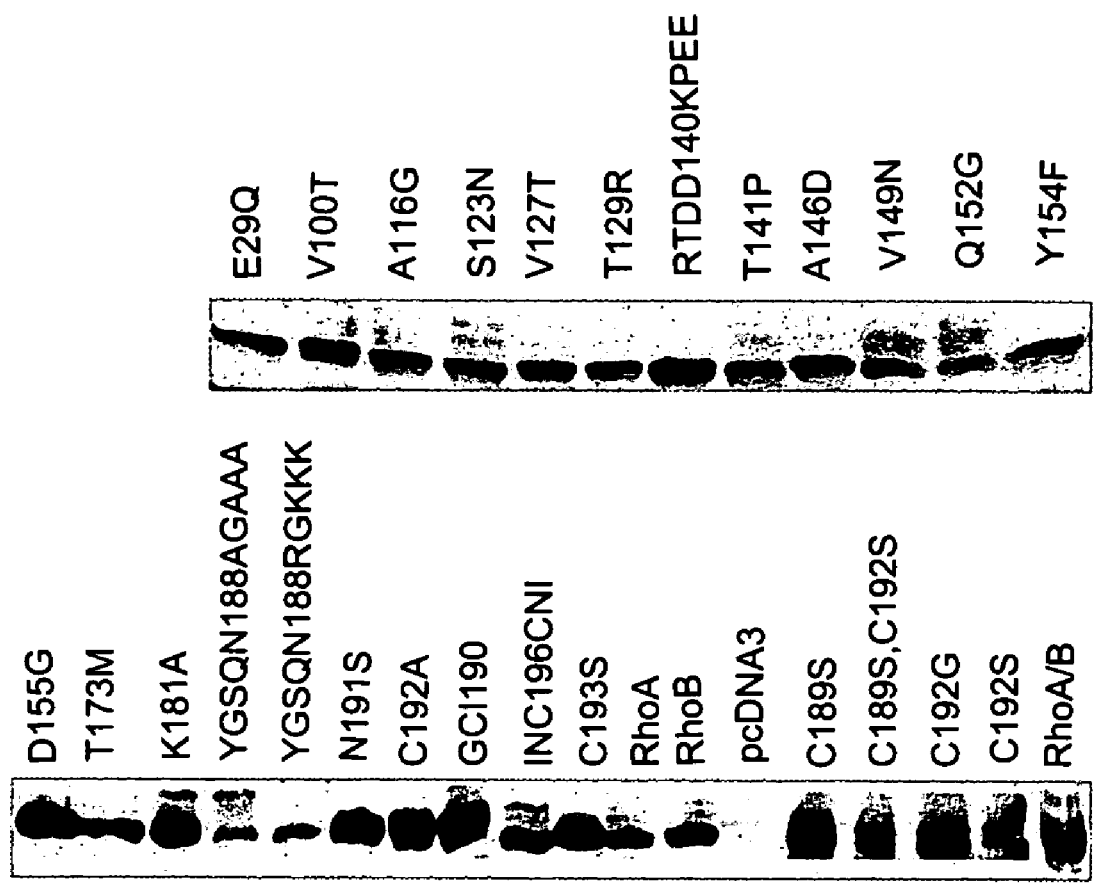

SEQ ID NOs:1-52 are forward and reverse primers used to generate RhoB variants of the invention.
SEQ ID NO:53 represents amino acids of human RhoA having sequence homology with RhoB.
SEQ ID NOs:54-57 represent amino acids of human RhoB having sequence homology with RhoA.

DETAILED DESCRIPTION OF THE INVENTION

In one aspect, the present invention provides a method of inhibiting the growth of cancerous cells by contacting the cells with an effective amount of a RhoB variant (also referred to herein as a "RhoB mutant"). Optionally, the cancerous cells can be contacted with the RhoB variant in combination (simultaneously or consecutively in any order) with one or more additional anti-cancer agents, such as cytotoxic agents (e.g., 5-flurouracil, TAXOL) and/or anti-signaling agents (e.g., the PI3K inhibitor LY). Advantageously, the RhoB variant can sensitize the cancerous cells to the activity of the anti-cancer agent. For example, the RhoB variant can act as a sensitizer to anti-cancer drug-induced apoptosis, or other anti-cancer activity.

The method of the present invention is useful for inhibiting the migration, invasion, and/or metastasis of cancer cells transformed by an oncogene such as H-Ras, N-Ras, K-Ras, EGFR, and ErbB2. The method of the present invention is useful for reducing malignant transformation of normal cells by these oncogenes.

In another aspect, the present invention concerns isolated RhoB variant polypeptides and isolated degenerate polynucleotides encoding the RhoB variant polypeptides. In another aspect, the present invention concerns nucleic acid constructs containing a polynucleotide encoding a RhoB variant polypeptide, and host cells genetically modified to express such polynucleotides.

The terms "RhoB variant" and "RhoB mutant" are used herein interchangeably and denote any variant of wild-type RhoB having altered structure (e.g., sequence) relative to the wild-type. Preferably, the RhoB variant possesses at least one characteristic biological activity of RhoB or RhoA. The variant may be derived from wild-type RhoB, for example, by truncation, oxidation, amino acid substitution, post-translational modification, labeling, or by linkage to another molecule. Exemplified RhoB variants are listed in Tables 2 and 3.

In one embodiment, the RhoB variant polypeptide of the invention has an amino acid sequence that is modified by one or more point mutations compared with the parent RhoB (the wild-type RhoB of a given organism, such as human). The human RhoB sequences were published by Chardin, P., et al. (*Nucleic Acids Res.* 1988, 16, 2717); Genbank accession number X06820 and CAA29968, which are incorporated herein by reference in their entirety.

A point mutation may be an insertion, substitution, or deletion of one or more amino acids within the coding sequence, for example. Preferably, the point mutation is a substitution of one or more amino acids (e.g., a substitution of one, two, three, four, or five or more amino acids at a given position). In one embodiment, the point mutation is at an amino acid position selected from the group consisting of 29, 100, 116, 123, 127, 129, 143, 141, 146, 149, 152, 154, 155, 173, 181, 187, 189, 190, 191, 192, and 193. In another embodiment, the RhoB variant polypeptide comprises two, three, four, or more point mutations. In a specific embodiment, the RhoB variant polypeptide comprises an amino acid sequence having one or more substitutions selected from the group consisting of those listed in Table 5, or a conservative substitution of the listed variants at the indicated amino acid positions.

In one embodiment, the RhoB variant is not RhoB-F or RhoB-GG. For the therapeutic methods of the invention, the RhoB variant preferably retains at least one characteristic biological activity of wild-type RhoB, such as p21waf and AP-1 promoter transcriptional activities, inhibition of anchorage-dependent and/or anchorage-independent tumor growth, and induction of apoptosis of cancerous cells.

In another aspect, the present invention provides polynucleotides, each comprising a nucleotide sequence encoding a RhoB variant polypeptide, each RhoB variant polypeptide having an amino acid sequence that is modified by one or more point mutations compared with the wild-type RhoB. The polynucleotides of the present invention include structurally conservative mutants. The terms "structurally conservative mutant" and "degenerate variant", as used herein, refer to a polynucleotide containing changes in the nucleic acid sequence but encoding a polypeptide having the same amino acid sequence as the polypeptide encoded by the polynucleotide from which the degenerate variant is derived. This can occur because a specific amino acid may be encoded by more than one codon (sequence of three nucleotides). Accordingly, the polynucleotides of the present include degenerate variants which, because of the degeneracy of the genetic code, have different nucleic acid sequences (i.e., one or more differing codons) from those polynucleotides exemplified herein, but which nonetheless encode the same amino acid sequences. A listing of valid codons for any given amino acid can be readily determined by those having knowledge of, or access to, the genetic code. Alternatively, so-called "back-translation" tools can be utilized to reverse-translate any given amino acid into its respective codons. One such tool is the "Utilities/Codon Calculator" feature of DNATOOLS for WINDOWS 95/98/NT/2000, which displays all possible degenerate codons for each amino acid input.

Unless otherwise indicated, a particular polynucleotide encoding a RhoB variant disclosed implicitly encompasses conservatively modified variants, degenerate variants, and full-length complementary sequences, as well as the sequence explicitly indicated.

Nomenclature for Amino Acids and Alterations

The specification refers to amino acids by their one-letter or three-letter codes. The following single-letter amino acid abbreviations are used throughout the text: Alanine: A; Arginine: R; Asparagine: N; Aspartic acid: D; Cysteine: C; Glutamine: Q; Glutamic acid: E; Glycine: G; Histidine: H; Isoleucine: I; Leucine: L; Lysine: K; Methionine: M; Phenylalanine: F; Proline: P; Serine: S; Threonine: T; Tryptophan: W; Tyrosine: Y; and Valine: V.

A particular amino acid in a sequence is identified by its one-letter code and its position, e.g., Q1 indicates Gln (glutamine at position 1, i.e., at the N-terminal). The nomenclature used herein for defining substitutions is the same as that used in the art. For example, C192S indicates substitution of C (Cys; cysteine) at position 192 with S (Ser; serine). C192S/G indicates substitution of C (Cys) at position 192 with S (Ser) or G (Gly; glycine), and so forth.

Homology and Alignment

For purposes of the present invention, the degree of homology (or identity) between wild-type RhoB and/or variant RhoB may be suitably determined according to the method described in Needleman, S. B. and Wunsch, C. D. *Journal of Molecular Biology*, 1970, 48:443-45, with the following settings for polypeptide sequence comparison: GAP creation penalty of 3.0 and GAP extension penalty of 0.1. The determination may be done by means of a computer program such as GAP provided in the GCG program package (Program Manual for the Wisconsin Package, Version 8, August 1994, Genetics Computer Group, 575 Science Drive, Madison, Wis., USA 53711).

Two given sequences can be aligned according to the method described in Needleman (supra) using the same parameters. This may be done by means of the GAP program (supra). The homology between the parent RhoB and the RhoB variant may be above 80%, e.g., above 85% or above 90%, particularly above 95%.

The present invention includes variants of RhoB that represent variants from any organism in which RhoB is found (e.g., mice, rats, humans, other mammals). A homologous nucleotide sequence, for the purposes of the present invention, encompasses a nucleotide sequence having a percentage identity with the bases of the nucleotide sequences of between at least (or at least about) 20.00% to 99.99% (inclusive). The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention. Homologous sequences exhibiting a percentage identity with residues of the amino acid sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the amino acid sequences of the instant invention. Homologous nucleotide and amino acid sequences include mammalian and non-mammalian homologues of the human RhoB polypeptide and nucleotide sequence encoding the human RhoB polypeptide. In a specific embodiment, the mammalian homologue is a nucleotide sequence encoding the human RhoB polypeptide. In another embodiment, the mammalian homologue is the amino acid sequence of the human RhoB polypeptide.

Hybridization

Suitable experimental conditions for determining hybridization at low, medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5× Denhardt's solution (Sambrook et al. 1989), 0.5% SDS and 100 µg/mi of denatured sonicated salmon sperm DNA (Sambrook et al. 1989), followed by hybridization in the same solution containing a random-primed (Feinberg, A. P. and Vogelstein, B. *Anal. Biochem.*, 1983, 132:6-13), $^{32}$P-dCTP-labeled (specific activity>1×10$^9$ cpm/µg) probe for 12 hours at ca. 45° C. The filter is then washed twice for 30 minutes in 2×SSC, 0.5% SDS at least *55° C. (low stringency), more preferably at least 60° C. (medium stringency), more preferably at least 65° C. (medium/high stringency), more preferably at least 70° C. (high stringency), even more preferably at least 75° C. (very high stringency). Molecules to which the oligonucleotide probe hybridizes under these conditions are detected using an x-ray film.

Specific Substitutions

The RhoB variants may particularly comprise one or more amino acid substitutions corresponding to the following positions in the human RhoB amino acid sequence (human RhoB numbering): 29, 100, 116, 123, 129, 141, 146, 149, 152, 154, 155, 173, 181, and 191. In another embodiment, the RhoB variant polypeptide comprises two, three, four, or more point mutations. In a specific embodiment, the RhoB variant polypeptide comprises an amino acid sequence having one or more substitutions selected from the group consisting of those listed in Table 5, or a conservative substitution of one or more of those listed in Table 5.

Nonclassical amino acids or chemical amino acid analogues can replace existing amino acid residues of RhoB or RhoB variant polypeptides, or be inserted into the RhoB variant polypeptides between existing amino acid residues of the RhoB or RhoB variant polypeptides or added to a terminus of the RhoB or RhoB variant polypeptides of the present invention. Non-classical amino acids include, but are not limited to, the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Furthermore, the amino acid can be D (dextrorotary) or L (levorotary). Dextrorotary amino acids are indicated herein by a parenthetical D, i.e., "(D)", immediately preceding the dextrorotary amino acid.

The RhoB variants of the invention include polypeptides containing, as a primary amino acid sequence, all or part of an exemplified RhoB variant polypeptide. The RhoB variants thus include RhoB variant polypeptides having conservative substitutions, i.e., altered sequences in which functionally equivalent amino acid residues are substituted for residues within the sequence resulting in a polypeptide which is functionally active. For example, one or more amino acid residues within the sequence can be substituted by another amino acid of a similar polarity which acts as a functional equivalent. In one aspect of the present invention, conservative substitutions for an amino acid within the sequence may be selected from other members of the class to which the amino acid belongs (see Table 1).

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Table 2 lists examples of RhoB variants of the subject invention and conservative substitutions which may be made to each to produce conservatively modified variants.

TABLE 2

| RhoB Variant | Conservative Substitutions |
|---|---|
| E29A | Val, Leu, Ile, Pro, Met, Phe, Trp |
| V100T | Gly, Ser, Cys, Tyr, Asn, Gln |
| A116G | Ser, Thr, Cys, Tyr, Asn, Gln |
| S123N | Gly, Ser, Thr, Cys, Tyr, Gln |
| V127T | Gly, Ser, Cys, Tyr, Asn, Gln |
| T129R | Lys, His |
| T141P | Ala, Val, Leu, Ile, Met, Phe, Trp |
| A146D | Glu |
| V149N | Gly, Ser, Thr, Cys, Tyr, Gln |
| Q152G | Ser, Thr, Cys, Tyr, Asn, Gln |
| Y154F | Ala, Val, Leu, Ile, Pro, Met, Trp |
| D155G | Ser, Thr, Cys, Tyr, Asn, Gln |
| T173M | Ala, Val, Leu, Ile, Pro, Phe, Trp |
| K181A | Val, Leu, Ile, Pro, Met, Phe, Trp |
| N191S | Gly, Thr, Cys, Tyr, Asn, Gln |
| C192A | Val, Leu, Ile, Pro, Met, Phe, Trp |
| C193S | Gly, Thr, Cys, Tyr, Asn, Gln |
| C192S | Gly, Thr, Cys, Tyr, Asn, Gln |
| C192G | Ser, Thr, Cys, Tyr, Asn, Gln |
| C189S | Gly, Thr, Cys, Tyr, Asn, Gln |

The present invention further includes fusion polypeptides (also referred to herein as chimeras or chimeric sequences), comprising one or more RhoB variants linked to a fusion partner, e.g., an effector molecule, a label, a drug, a toxin, an agent that increases polypeptide half-life in vivo, and/or a carrier or transport molecule. Techniques that may be utilized to couple RhoB variants of the invention to peptidyl or non-peptidyl fusion partners are well known in the art. In one embodiment, the fusion partner is at least a portion of RhoA, such as the chimera RhoA (1-180)/RhoB (181-196). In another embodiment, the fusion partner is an amino sequence derived from the homeodomain of Antennapedia (e.g., as sold under the name "Penetratin"), which can be coupled to a peptide via a terminal Cys residue, and operates as a carrier molecule. The "Penetratin" molecule and its properties are described in WO 91/18981. A RhoB variant polypeptide may be included within a fusion protein, where the RhoB variant is fused to the same RhoB variant sequence (as a multimer), or another RhoB variant sequence, or a non-RhoB variant sequence, such as a polypeptide or protein domain. Optionally, adjacent coding sequences can be separated by sequences that act as cleavage sites to endogenous or exogenous enzymes (the exogenous enzymes being provided concurrently or consecutively in any order).

RhoB variant polypeptides may be generated wholly or partly by chemical synthesis. The RhoB variant polypeptides of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they may be prepared in solution, by the liquid phase method or by any combination of solid-phase, liquid phase and solution.

Another convenient way of producing a RhoB variant polypeptide of the invention is to express nucleic acids encoding it, using the nucleic acids in an expression system.

Accordingly, the present invention also provides in various aspects nucleic acids encoding the RhoB variant polypeptides of the invention.

Generally, nucleic acids according to the present invention are provided as an isolate, in isolated and/or purified form, or free or substantially free of material with which it is naturally associated, such as free or substantially free of nucleic acid flanking the gene in the human genome, except possibly one or more regulatory sequences for expression. Nucleic acids may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding a RhoB polypeptide in accordance with the present invention can be readily prepared by the skilled person using the information and references contained herein and techniques known in the art (for example, see Sambrook, Fritsch and Maniatis, "Molecular Cloning, A Laboratory Manual", Cold Spring Harbor Laboratory Press, 1989, and Ausubel et al., Short Protocols in Molecular Biology, John Wiley and Sons, 1992), given the nucleic acid sequence and clones available. These techniques include (i) the use of the polymerase chain reaction (PCR) to amplify samples of such nucleic acid, e.g., from genomic sources, (ii) chemical synthesis, or (iii) preparing cDNA sequences. DNA encoding RhoB variant polypeptides may be generated and used in any suitable way known to those of skill in the art, including by taking encoding DNA, identifying suitable restriction enzyme recognition sites on either side of the portion to be expressed, and cutting out that portion from the DNA. The portion may then be operably linked to a suitable promoter in a standard commercially available expression system. Another recombinant approach is to amplify the relevant portion of the DNA with suitable PCR primers. Modifications to wild-type RhoB sequences can be made, e.g., using site directed mutagenesis, to lead to the expression of RhoB variants, or to take account of codon preference in the host cells used to express the nucleic acid.

In order to obtain expression of nucleic acid sequences encoding RhoB variant polypeptides, the sequences can be incorporated in a vector having one or more control sequences operably linked to the nucleic acid to control its expression. The vectors may include other sequences such as promoters or enhancers to drive the expression of the inserted nucleic acid, nucleic acid sequences so that the RhoB variant polypeptide is produced as a fusion and/or nucleic acid encoding secretion signals so that the polypeptide produced in the host cell is secreted from the cell. RhoB variant polypeptides can then be obtained by transforming the vectors into host cells in which the vector is functional, culturing the host cells so that the RhoB variant polypeptide is produced and recovering the RhoB variant polypeptide from the host cells or the surrounding medium. Prokaryotic and eukaryotic cells can be used for this purpose, including strains of E. coli, yeast, and eukaryotic cells such as COS or CHO cells.

Thus, the present invention also encompasses a method of making a RhoB variant polypeptide (as described herein), the method including expression from nucleic acid sencoding the RhoB variant polypeptide. This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is E. coli.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral, e.g., phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acids, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing heterologous nucleic acids encoding a RhoB variant polypeptide of the invention. The nucleic acids of the invention may be integrated into the genome (e.g., chromosome) of the host cell. Integration may be promoted by inclusion of sequences which promote recombination with the genome, in accordance with standard techniques. The nucleic acids may be on an extra-chromosomal vector within the cell, or otherwise identifiably heterologous or foreign to the cell.

A still further aspect provides a method which includes introducing the nucleic acids encoding a RhoB variant polypeptide into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g., vaccinia, adenovirus, adeno-associated virus, lentivirus, or, for insect cells, baculovirus. For bacterial cells, suitable techniques may include calcium chloride transformation, electroporation and transfection using bacteriophage. As an alternative, direct injection of the nucleic acids encoding the RhoB variant polypeptide (e.g., direct injection into a tumor) can be employed.

Marker genes such as antibiotic resistance or sensitivity genes may be used in identifying clones containing nucleic acid of interest, as is well known in the art.

The introduction may be followed by causing or allowing expression from the nucleic acids, e.g., by culturing host cells (which may include cells actually transformed although more likely the cells will be descendants of the transformed cells)

under conditions for expression of the gene, so that the encoded RhoB variant polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g., in the formulation of a composition which may include one or more additional components, such as a pharmaceutical composition which includes one or more pharmaceutically acceptable excipients, vehicles or carriers (as described in more detail below).

Introduction of nucleic acids encoding a RhoB variant polypeptide of the present invention may take place in vivo by way of gene therapy (e.g., to reduce the growth of cancer cells). Thus, a host cell containing nucleic acids according to the present invention, e.g., as a result of introduction of the nucleic acids into the cell or into an ancestor of the cell and/or genetic alteration of the sequence endogenous to the cell or ancestor (which introduction or alteration may take place in vivo or ex vivo), may be comprised within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

By inhibiting the growth of cancer cells, the methods and compositions of the present invention can be used to treat a number of cancers including, but no limited to, leukemias and lymphomas, such as acute lymphocytic leukemia, acute non-lymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms' Tumor, bone tumors, and soft-tissue sarcomas, common solid tumors of adults such as lung cancer, colon and rectum cancer, breast cancer, prostate cancer, urinary cancers, uterine cancers, bladder cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The methods of the subject invention can be carried out in vivo or in vitro, to inhibit the growth of cancerous cells in humans and non-human mammals.

RhoB variants of the present invention can be used to treat these cancers and other cancers at any stage from the discovery of the cancer to advanced stages. In addition, RhoB variants of the invention can be used in the treatment of the primary cancer and metastases thereof.

In other embodiments of the present invention, the RhoB variant polypeptides and nucleic acids encoding RhoB variant polypeptides described herein can be used for the treatment of cancer, including, but not limited to the cancers listed in Table 3 below.

TABLE 3

| Types of Cancer | |
|---|---|
| Acute Lymphoblastic Leukemia, Adult | Hairy Cell Leukemia |
| | Head and Neck Cancer |
| Acute Lymphoblastic Leukemia, Childhood | Hepatocellular (Liver) Cancer, Adult (Primary) |
| Acute Myeloid Leukemia, Adult | Hepatocellular (Liver) Cancer, Childhood (Primary) |
| Acute Myeloid Leukemia, Childhood | |
| Adrenocortical Carcinoma | Hodgkin's Lymphoma, Adult |
| Adrenocortical Carcinoma, Childhood | Hodgkin's Lymphoma, Childhood |
| | Hodgkin's Lymphoma During Pregnancy |
| AIDS-Related Cancers | Hypopharyngeal Cancer |
| AIDS-Related Lymphoma | Hypothalamic and Visual Pathway Glioma, Childhood |
| Anal Cancer | |
| Astrocytoma, Childhood Cerebellar | Intraocular Melanoma |
| Astrocytoma, Childhood Cerebral | Islet Cell Carcinoma (Endocrine Pancreas) |
| Basal Cell Carcinoma | Kaposi's Sarcoma |
| Bile Duct Cancer, Extrahepatic | Kidney (Renal Cell) Cancer |
| Bladder Cancer | Kidney Cancer, Childhood |
| Bladder Cancer, Childhood | Laryngeal Cancer |
| Bone Cancer, Osteosarcoma/Malignant Fibrous Histiocytoma | Laryngeal Cancer, Childhood |
| | Leukemia, Acute Lymphoblastic, Adult |
| | Leukemia, Acute Lymphoblastic, Childhood |
| Brain Stem Glioma, Childhood | |
| Brain Tumor, Adult | Leukemia, Acute Myeloid, Adult |
| Brain Tumor, Brain Stem Glioma, Childhood | Leukemia, Acute Myeloid, Childhood |
| | Leukemia, Chronic Lymphocytic |
| Brain Tumor, Cerebellar Astrocytoma, Childhood | Leukemia, Chronic Myelogenous |
| | Leukemia, Hairy Cell |
| Brain Tumor, Cerebral Astrocytoma/Malignant Glioma, Childhood | Lip and Oral Cavity Cancer |
| | Liver Cancer, Adult (Primary) |
| | Liver Cancer, Childhood (Primary) |
| Brain Tumor, Ependymoma, Childhood | Lung Cancer, Non-Small Cell |
| | Lung Cancer, Small Cell |
| Brain Tumor, Medulloblastoma, Childhood | Lymphoma, AIDS-Related |
| | Lymphoma, Burkitt's |
| Brain Tumor, Supratentorial Primitive Neuroectodermal Tumors, Childhood | Lymphoma, Cutaneous T-Cell, see Mycosis Fungoides and Sézary Syndrome |
| | Lymphoma, Hodgkin's, Adult |
| Brain Tumor, Visual Pathway and Hypothalamic Glioma, Childhood | Lymphoma, Hodgkin's, Childhood |
| | Lymphoma, Hodgkin's During Pregnancy |
| Brain Tumor, Childhood | Lymphoma, Non-Hodgkin's, Adult |
| Breast Cancer | Lymphoma, Non-Hodgkin's, Childhood |
| Breast Cancer, Childhood | Lymphoma, Non-Hodgkin's During |

TABLE 3-continued

| Types of Cancer | |
|---|---|
| Breast Cancer, Male | Pregnancy |
| Bronchial Adenomas/Carcinoids, Childhood | Lymphoma, Primary Central Nervous System |
| Burkitt's Lymphoma | Macroglobulinemia, Waldenström's |
| Carcinoid Tumor, Childhood | Malignant Fibrous Histiocytoma of Bone/Osteosarcoma |
| Carcinoid Tumor, Gastrointestinal | |
| Carcinoma of Unknown Primary | Medulloblastoma, Childhood |
| Central Nervous System Lymphoma, Primary | Melanoma |
| | Melanoma, Intraocular (Eye) |
| Cerebellar Astrocytoma, Childhood | Merkel Cell Carcinoma |
| Cerebral Astrocytoma/Malignant Glioma, Childhood | Mesothelioma, Adult Malignant |
| | Mesothelioma, Childhood |
| Cervical Cancer | Metastatic Squamous Neck Cancer with Occult Primary |
| Childhood Cancers | |
| Chronic Lymphocytic Leukemia | Multiple Endocrine Neoplasia Syndrome, Childhood |
| Chronic Myelogenous Leukemia | |
| Chronic Myeloproliferative Disorders | Multiple Myeloma/Plasma Cell Neoplasm |
| Colon Cancer | Mycosis Fungoides |
| Colorectal Cancer, Childhood | Myelodysplastic Syndromes |
| Cutaneous T-Cell Lymphoma, see Mycosis Fungoides and Sézary Syndrome | Myelodysplastic/Myeloproliferative Diseases |
| | Myelogenous Leukemia, Chronic |
| Endometrial Cancer | Myeloid Leukemia, Adult Acute |
| Ependymoma, Childhood | Myeloid Leukemia, Childhood Acute |
| Esophageal Cancer | Myeloma, Multiple |
| Esophageal Cancer, Childhood | Myeloproliferative Disorders, Chronic |
| Ewing's Family of Tumors | Nasal Cavity and Paranasal Sinus Cancer |
| Extracranial Germ Cell Tumor, Childhood | Nasopharyngeal Cancer |
| | Nasopharyngeal Cancer, Childhood |
| Extragonadal Germ Cell Tumor | Neuroblastoma |
| Extrahepatic Bile Duct Cancer | Non-Hodgkin's Lymphoma, Adult |
| Eye Cancer, Intraocular Melanoma | Non-Hodgkin's Lymphoma, Childhood |
| Eye Cancer, Retinoblastoma | Non-Hodgkin's Lymphoma During Pregnancy |
| Gallbladder Cancer | |
| Gastric (Stomach) Cancer | Non-Small Cell Lung Cancer |
| Gastric (Stomach) Cancer, Childhood | Oral Cancer, Childhood |
| Gastrointestinal Carcinoid Tumor | Oral Cavity Cancer, Lip and Oropharyngeal Cancer |
| Germ Cell Tumor, Extracranial, Childhood | |
| | Osteosarcoma/Malignant Fibrous Histiocytoma of Bone |
| Germ Cell Tumor, Extragonadal | Ovarian Cancer, Childhood |
| Germ Cell Tumor, Ovarian | Ovarian Epithelial Cancer |
| Gestational Trophoblastic Tumor | Ovarian Germ Cell Tumor |
| Glioma, Adult | Ovarian Low Malignant Potential Tumor |
| Glioma, Childhood Brain Stem | Pancreatic Cancer |
| Glioma, Childhood Cerebral Astrocytoma | Pancreatic Cancer, Childhood |
| | Pancreatic Cancer, Islet Cell |
| Glioma, Childhood Visual Pathway and Hypothalamic | Paranasal Sinus and Nasal Cavity Cancer |
| | Parathyroid Cancer |
| Skin Cancer (Melanoma) | Penile Cancer |
| Skin Carcinoma, Merkel Cell | Pheochromocytoma |
| Small Cell Lung Cancer | Pineoblastoma and Supratentorial Primitive Neuroectodermal Tumors, Childhood |
| Small Intestine Cancer | |
| Soft Tissue Sarcoma, Adult | Pituitary Tumor |
| Soft Tissue Sarcoma, Childhood | Plasma Cell Neoplasm/Multiple Myeloma |
| Squamous Cell Carcinoma, see Skin Cancer (non-Melanoma) | Pleuropulmonary Blastoma |
| | Pregnancy and Breast Cancer |
| Squamous Neck Cancer with Occult Primary, Metastatic | Pregnancy and Hodgkin's Lymphoma |
| | Pregnancy and Non-Hodgkin's Lymphoma |
| Stomach (Gastric) Cancer | Primary Central Nervous System Lymphoma |
| Stomach (Gastric) Cancer, Childhood | |
| Supratentorial Primitive Neuroectodermal Tumors, Childhood | Prostate Cancer |
| | Rectal Cancer |
| T-Cell Lymphoma, Cutaneous, see Mycosis Fungoides and Sézary Syndrome | Renal Cell (Kidney) Cancer |
| | Renal Cell (Kidney) Cancer, Childhood |
| | Renal Pelvis and Ureter, Transitional Cell Cancer |
| Testicular Cancer | |
| Thymoma, Childhood | Retinoblastoma |
| Thymoma and Thymic Carcinoma | Rhabdomyosarcoma, Childhood |
| Thyroid Cancer | Salivary Gland Cancer |
| Thyroid Cancer, Childhood | Salivary Gland Cancer, Childhood |
| Transitional Cell Cancer of the Renal Pelvis and Ureter | Sarcoma, Ewing's Family of Tumors |
| | Sarcoma, Kaposi's |
| Trophoblastic Tumor, Gestational | Sarcoma, Soft Tissue, Adult |
| Unknown Primary Site, Carcinoma of, Adult | Sarcoma, Soft Tissue, Childhood |
| | Sarcoma, Uterine |
| Unknown Primary Site, Cancer of, Childhood | Sezary Syndrome |
| | Skin Cancer (non-Melanoma) |

TABLE 3-continued

Types of Cancer

| | |
|---|---|
| Unusual Cancers of Childhood | Skin Cancer, Childhood |
| Ureter and Renal Pelvis, Transitional Cell Cancer | |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

In another aspect, the present invention provides a method of reducing malignant transformation of a cell. In this embodiment, a RhoB variant or a composition comprising a RhoB variant is administered to a cell capable of malignant transformation, thereby inhibiting transformation. The method of the invention may prevent malignant transformation of the cell.

As demonstrated herein, the present invention further provides a method of inducing apoptosis in transformed cells. In this embodiment, a RhoB variant or a composition including a RhoB variant is administered to the transformed cells, thereby promoting apoptosis.

In another aspect of the invention, the therapeutic methods of the invention can be advantageously combined with at least one additional therapeutic technique, including but not limited to chemotherapy, radiation therapy, surgery (e.g., surgical excision of cancerous or pre-cancerous cells), therapy that selectively inhibits Ras oncogenic signaling, or any other therapy known to those of skill in the art of the treatment and management of cancer, such as administration of an anti-cancer agent. Examples of Ras oncogenic signaling agents include those described in Reuter C. W. M. et al., "Targeting the Ras signaling pathway: a rational, mechanism-based treatment for hematologic malignancies", *Blood*, 1 Sep. 2000, 95(5):1655-1669; and Adjei A. A. et al., "Ras Signaling Pathway Proteins as Therapeutic Targets", *Current Pharmaceutical Design*, 2001, 7:1781-1594, which are incorporated herein by reference in their entirety.

The RhoB variants and compositions disclosed herein can be combined with at least one additional chemotherapeutic agent. The additional agents can be administered in combination or alternation with the RhoB variants disclosed herein. The RhoB variant and additional agent can form part of the same composition, or be provided as a separate composition for administration at the same time or a different time.

In one embodiment, compounds disclosed herein can be combined with agents, such as cytotoxic agents, to enhance their effectiveness. In another embodiment, the RhoB variants and compositions, when used in the treatment of solid tumors, can be administered with the agents selected from, but not limited to IL-12, retinoids, interferons, angiostatin, endostatin, thalidomide, thrombospondin-1, thrombospondin-2, captopryl, anti-neoplastic agents such as alpha interferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and radiation. In further embodiments, the RhoB variants and compositions disclosed herein can be administered in combination or alternation with, for example, drugs with antimitotic effects, such as those which target cytoskeletal elements, including microtubule modulators such as taxane drugs (such as taxol, paclitaxel, taxotere, docetaxel), podophylotoxins or vinca alkaloids (vincristine, vinblastine); antimetabolite drugs (such as 5-fluorouracil, cytarabine, gemcitabine, purine analogues such as pentostatin, methotrexate); alkylating agents or nitrogen mustards (such as nitrosoureas, cyclophosphamide or ifosphamide); drugs which target DNA such as the antracycline drugs adriamycin, doxorubicin, pharmorubicin or epirubicin; drugs which target topoisomerases such as etoposide; hormones and hormone agonists or antagonists such as estrogens, antiestrogens (tamoxifen and related compounds) and androgens, flutamide, leuprorelin, goserelin, cyprotrone or octreotide; drugs which target signal transduction in tumour cells including antibody derivatives such as herceptin; alkylating drugs such as platinum drugs (cis-platin, carbonplatin, oxaliplatin, paraplatin) or nitrosoureas; drugs potentially affecting metastasis of tumours such as matrix metalloproteinase inhibitors; gene therapy and antisense agents; antibody therapeutics; other bioactive compounds of marine origin, notably the didemnins such as aplidine; steroid analogues, in particular dexamethasone; anti-inflammatory drugs, including nonsteroidal agents (such as acetaminophen or ibuprofen) or steroids and their derivatives in particular dexamethasone; anti-emetic drugs, including 5HT-3 inhibitors (such as gramisetron or ondasetron), and steroids and their derivatives in particular dexamethasone. In still further embodiments, the RhoB variants and compositions can be used in combination or alternation with the chemotherapeutic agents listed below in Table 4.

TABLE 4

| Chemotherapeutic Agents | |
|---|---|
| 13-cis-Retinoic Acid | Neosar |
| 2-Amino-6-Mercaptopurine | Neulasta |
| | Neumega |
| 2-CdA | Neupogen |
| 2-Chlodeoxyadenosine | Nilandron |
| 5-fluorouracil | Nilutamide |
| 5-FU | Nitrogen Mustard |
| 6-TG | Novaldex |
| 6-Thioguanine | Novantrone |
| 6-Mercaptopurine | Octreotide |
| 6-MP | Octreotide acetate |
| Accutane | Oncospar |
| Actinomycin-D | Oncovin |
| Adriamycin | Ontak |
| Adrucil | Onxal |

TABLE 4-continued

Chemotherapeutic Agents

| | |
|---|---|
| Agrylin | Oprevelkin |
| Ala-Cort | Orapred |
| Aldesleukin | Orasone |
| Alemtuzumab | Oxaliplatin |
| Alitretinoin | Paclitaxel |
| Alkaban-AQ | Pamidronate |
| Alkeran | Panretin |
| All-transretinoic acid | Paraplatin |
| Alpha interferon | Pediapred |
| Altretamine | PEG Interferon |
| Amethopterin | Pegaspargase |
| Amifostine | Pegfilgrastim |
| Aminoglutethimide | PEG-INTRON |
| Anagrelide | PEG-L-asparaginase |
| Anandron | Phenylalanine Mustard |
| Anastrozole | Platinol |
| Arabinosylcytosine | Platinol-AQ |
| Ara-C | Prednisolone |
| Aranesp | Prednisone |
| Aredia | Prelone |
| Arimidex | Procarbazine |
| Aromasin | PROCRIT |
| Arsenic trioxide | Proleukin |
| Asparaginase | Prolifeprospan 20 with Carmustine implant |
| ATRA | Purinethol |
| Avastin | Raloxifene |
| BCG | Rheumatrex |
| BCNU | Rituxan |
| Bevacizumab | Rituximab |
| Bexarotene | Roveron-A (interferon alfa-2a) |
| Bicalutamide | Rubex |
| BiCNU | Rubidomycin hydrochloride |
| Blenoxane | Sandostatin |
| Bleomycin | Sandostatin LAR |
| Bortezomib | Sargramostim |
| Busulfan | Solu-Cortef |
| Busulfex | Solu-Medrol |
| C225 | STI-571 |
| Calcium Leucovorin | Streptozocin |
| Campath | Tamoxifen |
| Camptosar | Targretin |
| Camptothecin-11 | Taxol |
| Capecitabine | Taxotere |
| Carac | Temodar |
| Carboplatin | Temozolomide |
| Carmustine | Teniposide |
| Carmustine wafer | TESPA |
| Casodex | Thalidomide |
| CCNU | Thalomid |
| CDDP | TheraCys |
| CeeNU | Thioguanine |
| Cerubidine | Thioguanine Tabloid |
| cetuximab | Thiophosphoamide |
| Chlorambucil | Thioplex |
| Cisplatin | Thiotepa |
| Citrovorum Factor | TICE |
| Cladribine | Toposar |
| Cortisone | Topotecan |
| Cosmegen | Toremifene |
| CPT-11 | Trastuzumab |
| Cyclophosphamide | Tretinoin |
| Cytadren | Trexall |
| Cytarabine | Trisenox |
| Cytarabine liposomal | TSPA |
| Cytosar-U | VCR |
| Cytoxan | Velban |
| Dacarbazine | Velcade |
| Dactinomycin | VePesid |
| Darbepoetin alfa | Vesanoid |
| Daunomycin | Viadur |
| Daunorubicin | Vinblastine |
| Daunorubicin hydrochloride | Vinblastine Sulfate |
| | Vincasar Pfs |
| Daunorubicin liposomal | Vincristine |
| DaunoXome | Vinorelbine |
| Decadron | Vinorelbine tartrate |
| Delta-Cortef | VLB |
| Deltasone | VP-16 |
| Denileukin diftitox | Vumon |
| DepoCyt | Xeloda |
| Dexamethasone | Zanosar |
| Dexamethasone acetate | Zevalin |
| dexamethasone sodium phosphate | Zinecard |
| | Zoladex |
| Dexasone | Zoledronic acid |
| Dexrazoxane | Zometa |
| DHAD | Gliadel wafer |
| DIC | Glivec |
| Diodex | GM-CSF |
| Docetaxel | Goserelin |
| Doxil | granulocyte - colony stimulating factor |
| Doxorubicin | Granulocyte macrophage colony stimulating factor |
| Doxorubicin liposomal | |
| Droxia | Halotestin |
| DTIC | Herceptin |
| DTIC-Dome | Hexadrol |
| Duralone | Hexalen |
| Efudex | Hexamethylmelamine |
| Eligard | HMM |
| Ellence | Hycamtin |
| Eloxatin | Hydrea |
| Elspar | Hydrocort Acetate |
| Emcyt | Hydrocortisone |
| Epirubicin | Hydrocortisone sodium phosphate |
| Epoetin alfa | Hydrocortisone sodium succinate |
| Erbitux | Hydrocortone phosphate |
| Erwinia L-asparaginase | Hroxyurea |
| Estramustine | Ibritumomab |
| Ethyol | Ibritumomab Tiuxetan |
| Etopophos | Idamycin |
| Etoposide | Idarubicin |
| Etoposide phosphate | Ifex |
| Eulexin | IFN-alpha |
| Evista | Ifosfamide |
| Exemestane | IL-2 |
| Fareston | IL-11 |
| Faslodex | Imatinib mesylate |
| Femara | Imidazole Carboxamide |
| Filgrastim | Interferon alfa |
| Floxuridine | Interferon Alfa-2b (PEG conjugate) |
| Fludara | Interleukin-2 |
| Fludarabine | Interleukin-11 |
| Fluoroplex | Intron A (interferon alfa-2b) |
| Fluorouracil | Leucovorin |
| Fluorouracil (cream) | Leukeran |
| Fluoxymesterone | Leukine |
| Flutamide | Leuprolide |
| Folinic Acid | Leurocristine |
| FUDR | Leustatin |
| Fulvestrant | Liposomal Ara-C |
| G-CSF | Liquid Pred |
| Gefitinib | Lomustine |
| Gemcitabine | L-PAM |
| Gemtuzumab ozogamicin | L-Sarcolysin |
| Gemzar | Meticorten |
| Gleevec | Mitomycin |
| Lupron | Mitomycin-C |
| Lupron Depot | Mitoxantrone |
| Matulane | M-Prednisol |
| Maxidex | MTC |
| Mechlorethamine | MTX |
| Mechlorethamine Hydrochlorine | Mustargen |
| | Mustine |
| Medralone | Mutamycin |
| Medrol | Myleran |
| Megace | Iressa |
| Megestrol | Irinotecan |
| Megestrol Acetate | Isotretinoin |
| Melphalan | Kidrolase |
| Mercaptopurine | Lanacort |
| Mesna | L-asparaginase |
| Mesnex | LCR |

TABLE 4-continued

Chemotherapeutic Agents

Methotrexate
Methotrexate Sodium
Methylprednisolone
Mylocel
Letrozole

Patients in need of treatment using the methods of the present invention can be identified using standard techniques known to those in the medical profession.

The methods of the present invention can be performed by introducing a nucleic acid construct encoding the RhoB variant polypeptide into the cell, whereby the nucleic acid is expressed and the RhoB variant polypeptide is made within the cell from the construct. The term "nucleic acid construct" refers to an assembly which is capable of directing the expression of the sequence(s) or gene(s) of interest. The construct preferably includes transcriptional promoter/enhancer or locus defining element(s), or other elements which control gene expression by other means such as alternate splicing, nuclear RNA export, post-translational modification of messenger, or post-transcriptional modification of protein. In addition, the construct preferably includes a sequence which, when transcribed, is operably linked to the sequence(s) or gene(s) of interest and acts as a translation initiation sequence. Optionally, the vector construct may also include a signal which directs polyadenylation, a selectable marker such as Neo, TK, hygromycin, phleomycin, histidinol, or DHFR, as well as one or more restriction sites and a translation termination sequence. In addition, if the vector construct is placed into a retrovirus, the vector construct preferably includes a packaging signal, long terminal repeats (LTRs), and positive and negative strand primer binding sites appropriate to the retrovirus used (if these are not already present).

Within one embodiment, a recombinant viral vector (preferably, but not necessarily, a recombinant adenovirus) carries a vector construct containing a RhoB variant encoding nucleic acid sequence operably linked with a promoter, such as an event-specific promoter, which will be transcriptionally active in cancerous cells. An example of an event-specific promoter is a cell cycle-dependent promoter (e.g., human cellular thymidine kinase or transferrin receptor promoters), which will be transcriptionally active primarily in rapidly proliferating cells, such as tumors. In this manner, rapidly replicating cells that contain factors capable of activating transcription from these promoters are preferentially destroyed by the RhoB variant produced by the vector construct.

Administration of the RhoB variant as a salt may be carried out. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The RhoB variant polypeptides, or nucleic acids that encode them, can be formulated as pharmaceutical compositions and administered to a patient, such as a human patient, in a variety of forms adapted to the chosen route of administration, i.e., orally or parenterally, by intravenous, intramuscular, topical or subcutaneous routes, or via electroporation, or transformation. Additionally, naked DNA, or via virally mediated administration may be employed. In one embodiment, the RhoB variant polypeptide, or nucleic acids encoding it, is administered locally, directly at the site or sites of the cancerous cells. For example, the RhoB variant polypeptide, or nucleic acids encoding it, can be administered directly at the site of a tumor (intratumorally).

Thus, the RhoB variants (i.e., polypeptides or polynucleotides encoding the polypeptides) may be systemically administered, e.g., orally, in combination with a pharmaceutically acceptable vehicle (i.e., carrier) such as an inert diluent or an assimilable edible carrier. Such compositions and preparations should contain at least 0.1% of active agent. The percentage of the compositions and preparations may, of course, be varied and may conveniently be between about 2 to about 60% of the weight of a given unit dosage form. The amount of RhoB variant in such therapeutically useful compositions is such that an effective dosage level will be obtained at the site or sites of cancerous cells.

The pharmaceutical composition may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the RhoB or RhoB variant, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the RhoB variant (i.e., polypeptides or polynucleotides encoding the polypeptides) may be incorporated into sustained-release preparations and devices.

The active agent (i.e., RhoB variant polypeptides or polynucleotides encoding the polypeptides) may also be administered intravenously or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the RhoB variant (i.e., polypeptides or polynucleotides encoding the polypeptides) in the required amount in the appropriate solvent with various other ingredients such as those enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the RhoB variants may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the RhoB or RhoB variants can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the RhoB variant to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the active agent in a liquid composition, such as a lotion, will be from about 0.1-25 wt.-%, preferably from about 0.5-10 wt.-%. The concentration in a semi-solid or solid composition such as a gel or a powder will be about 0.1-5 wt.-%, preferably about 0.5-2.5 wt.-%. Single dosages for injection, infusion or ingestion will generally vary between 5-1500 mg, and may be administered, i.e., 1-3 times daily, to yield levels of about 0.1-50 mg/kg, for adults. A preferred dosage of the present invention is between 7.5 to 45 mg per day, administered orally, with appropriate adjustment for the body weight of an individual.

Accordingly, the present invention includes a pharmaceutical composition comprising one or more RhoB variants as described herein, in combination with a pharmaceutically acceptable carrier. Pharmaceutical compositions adapted for local, enteral (e.g., nasal or oral), topical, or parenteral administration, comprising an amount of RhoB variant constitute a preferred embodiment of the invention. The dose administered to a patient, particularly a human, in the context of the present invention should be sufficient to achieve a therapeutic response in the patient over a reasonable time frame. One skilled in the art will recognize that the dosage will depend upon a variety of factors including the condition of the patient, the body weight of the patient, as well as the severity and stage of the cancer.

A suitable dose is that which will result in a concentration of the active agent in cancerous tissue (e.g., tumor tissue) which is known to achieve the desired response. The preferred dosage is the amount which results in maximum reduction of cancer cell growth, without unmanageable side effects. Administration of RhoB variant polypeptide or a nucleic acid sequence encoding RhoB variant polypeptide can be continuous or at distinct intervals, as can be determined by a person of ordinary skill in the art.

Mammalian species which benefit from the disclosed methods for the reduction of cancer cell growth (e.g., via induction of apoptosis), malignant cell transformation, and oncogenic signaling, include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. As used herein, the terms "patient" and "subject" are intended to include such human and non-human mammalian species. Preferably, the RhoB variant administered to a particular subject represents a variant of the RhoB that naturally occurs in the particular species. For example, if the subject is a human, a variant of the human wild-type RhoB sequence is used. Likewise, in vitro methods of the present invention can be carried out on cells of such mammalian species. For in vitro therapeutic methods, polynucleotides encoding the RhoB variant polypeptides can be introduced into host cells (autologous, allogenic, or xenogenic cells) ex vivo, and the cells can be administered to the patient. The RhoB variant-encoding polynucleotides are then expressed at the cancerous site or sites. Optionally, the host cells can be seeded onto a scaffold prior to implantation of the scaffold on or within the patient.

Patients in need of treatment using the methods of the present invention can be identified using standard techniques known to those in the medical profession. For the therapeutic methods of the invention, RhoB variants can be derived from wild-type RhoB of various organisms. Preferably, the RhoB variant is a variant of the wild-type RhoB of the patient. For example, if the patient is human, the RhoB variant administered to the patient is preferably a variant of human RhoB.

Various viral and non-viral vectors may be used to deliver nucleic acids encoding RhoB variant polypeptides to cancerous cells, resulting in RhoB variant expression (see, for example, Patil S. D. et al., *The AAPS Journal*, 2005, 7(1), Article 9, which is incorporated herein by reference in its entirety, for a review of DNA delivery systems). Tissue-specific promoters or event-specific promoters may be utilized with nucleic acids encoding RhoB variants to further optimize and localize expression within the diseased tissues. Various methodologies and vectors are available for delivering and expressing a polynucleotide in vivo for the purpose of treating cancer (Robson, T. Hirst, D. G., *J. Biomed and Biotechnol.*, 2003, 2003(2): 110-137), which is incorporated herein by reference in its entirety. Among the various targeting techniques available, transcriptional targeting using tissue-specific and event-specific transcriptional control elements is discussed. For example, in Table 1 of Robson et al. publication, several tissue-specific promoters useful in cancer therapy are listed. Tables 2-4 of Robson et al. list tumor-specific promoters, tumor environment-specific promoters, and exogenously controlled inducible promoters, which may utilized with the invention. The successful delivery and expression of the p53 tumor suppressor gene in vivo has been documented (Horowitz, J. *Curr. Opin. Mol. Ther.*, 1999, 1(4): 500-509; Von Gruenigen, V. E. et al. *Int. J. Gynecol. Cancer*, 1999, 9(5):365-372; Fujiwara, T. et al., *Mol. Urol.*, 2000, 4(2):51-54, respectively). Chronic gene delivery of interferon-inducible protein 10 using replication-competent retrovirus vectors resulted in suppressed tumor growth (Sun Y. et al., *Cancer Gene Therapy*, 2005, 12:900-912).

Other techniques may be used to deliver RhoB variant polypeptides of the invention to cancer cells. For example, RhoB variants of the invention can be coupled to sequences that act as carrier molecules for the RhoB variant (as fusion polypeptides). Peptides known as "cell penetrating peptides" (CPP) or "protein transduction domains" (PTD) have an ability to cross the cell membrane and enter the cell. PTDs can be linked to a cargo moiety such as a drug, peptide, or full-length protein, and can transport the moiety across the cell membrane. One well characterized PTD is the human immunodeficient virus (HIV)-1 Tat peptide (see, for example, Frankel et al., U.S. Pat. Nos. 5,804,604; 5,747,641; 5,674,980; 5,670,617; and 5,652,122; Fawell, S. et al., *Proc. Natl. Acad. Sci. U.S.A.*, 1994, 91:664-668). Peptides such as the homeodomain of *Drosophila* antennapedia (ANTp) and arginine-rich peptides display similar properties (Derossi, D. et al., *J. Biol. Chem.*, 1994, 269:10444-10450; Derossi, D. et al., *Trends Cell Biol.*, 1998, 8:84-87; Rojas, M. et al., *Nat. Biotechnol.*, 1998, 16:370-375; Futaki, S. et al., *J. Biol. Chem.*, 2001, 276:5836-5840). A protein delivery system using 11 poly-arginine peptides has been used for the transduction of the tumor suppressor protein, p53, to suppress the proliferation of oral cancer cells, with the effect equivalent to that of the adenovirus-mediated p53 gene transduction system (Takenobu T. et al., *Molecular Cancer Therapeutics*, 2002, 1:1043-1049). VP22, a tegument protein from Herpes simplex virus type 1 (HSV-1), also has the ability to transport proteins across a cell membrane (Elliot et al., *Cell*, 1997, 88:223-233; Schwarze S. R. et al., *Trends Pharmacol. Sci.*, 2000, 21:45-48). A common feature of these carriers is that they are highly basic and hydrophilic (Schwarze S. R. et al., *Trends Cell Biol.*, 2000, 10:290-295). Coupling of these carriers to marker proteins such as beta-galactosidase has been shown to confer efficient internalization of the marker protein into cells. More recently, chimeric, in-frame fusion proteins containing these carriers have been used to deliver proteins to a wide spectrum of cell types both in vitro and in vivo. For example, VP22-p53 chimeric protein retained its ability to spread between cells and its pro-apoptotic activity, and had a widespread cytotoxic effect in p53 negative human osteosarcoma cells in vitro (Phelan, A. et al., *Nature Biotechnol.*, 1998, 16:440-443). Intraperitoneal injection of the beta-galactosidase protein fused to the HIV-1 Tat peptide resulted in delivery of the biologically active fusion protein to all tissues in mice, including the brain (Schwarze S. R. et al., *Science*, 1999, 285:1569-1572). Liposomes of various compositions can also be used for site-specific delivery of proteins and drugs (Witschi, C. et al., *Pharm. Res.*, 1999, 16:382-390; Yeh, M. K. et al., *Pharm. Res.*, 1996, 1693-1698). The interaction between the liposomes and the protein cargo usually relies on hydrophobic interactions or charge attractions, particularly in the case of cationic lipid delivery systems (Zelphati, O. et al., *J. Biol. Chem.*, 2001, 276:35103-35110). Tat peptide-bearing liposomes have also been constructed and used to deliver cargo directly into the cytoplasm, bypassing the endocytotic pathway (Torchilin V. P. et al., *Biochim. Biophys. Acta-Biomembranes*, 2001, 1511:397-411; Torchilin V. P. et al., *Proc. Natl. Acad. Sci. USA*, 2001, 98:8786-8791). When encapsulated in sugar-grafted liposomes, pentamidine isethionate and a derivative have been found to be more potent in comparison to normal liposome-encapsulated drug or to the free drug (Banerjee, G. et al., *J. Antimicrob. Chemother.*, 1996, 38(1):145-150). A thermo-sensitive liposomal taxol formulation (heat-mediated targeted drug delivery) has been administered in vivo to tumor-bearing mice in combination with local hyperthermia, and a significant reduction in tumor volume and an increase in survival time was observed compared to the equivalent dose of free taxol with or without hyperthermia (Sharma, D. et al., *Melanoma Res.*, 1998, 8(3): 240-244). Topical application of liposome preparations for delivery of insulin, IFN-alpha, IFN-gamma, and prostaglandin E1 have met with some success (Cevc G. et al., *Biochim. Biophys, Acta*, 1998, 1368:201-215; Foldvari M. et al., *J. Liposome Res.*, 1997, 7:115-126; Short S. M. et al., *Pharm. Res.*, 1996, 13:1020-1027; Foldvari M. et al., *Urology*, 1998, 52(5):838-843; U.S. Pat. No. 5,853,755). Antibodies represent another targeting device that may make liposome uptake tissue-specific or cell-specific (Mastrobattista, E. et al., *Biochim. Biophys. Acta*, 1999, 1419(2):353-363; Mastrobattista, E. et al., *Adv. Drug Deliv. Rev.*, 1999, 40(1-2):103-127). The liposome approach offers several advantages, including the ability to slowly release encapsulated drugs and proteins, the capability of evading the immune system and proteolytic enzymes, and the ability to be targeted to tumors and preferentially accumulate in tumor tissues and their metastases by extravasation through their leaky neovasculature. Other carriers have also been used to deliver anti-cancer drugs to neoplastic cells, such as polyvinylpyrrolidone nanoparticles and maleylated bovine serum albumin (Sharma, D. et al., *Oncol. Res.*, 1996, 8(7-8):281-286; Mukhopadhyay, A. et al., *FEBS Lett.*, 1995, 376(1-2):95-98). Targeting systems for cancer treatments, such as nanoparticles composed of degradable and nondegradable polymers are described in Brannon-Peppas L. and Blanchette J. O., *Advanced Drug Delivery Reviews*, 2004, 56:1649-1659; Kwok K. K., *The Annals of Pharmacotherapy*, 2004, 38(6):1095-1096; and Minko T et al., *Current Drug Targets*, 2004, 5(4):389-406(18). Thus, using targeting and encapsulation technologies, which are very versatile and amenable to rational design and modification, the delivery of RhoB variant polypeptides of the invention to cancerous cells can be facilitated. Furthermore, because many liposome compositions are also viable delivery vehicles for genetic material, many of the advantages of liposomes are equally applicable to nucleic acid sequences encoding RhoB variants of the invention.

In addition to therapy, RhoB variants of the present invention may be used in vivo or in vitro for oncology research, such as the study of tumorigenesis and oncological signaling (such as in vitro chemosensitivity and chemoresistance assays, colon-forming assays, DNA synthesis-based assays, and use of animal models).

As used herein, the terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

As used herein, the term "metastasis" refers to the process by which cancer cells are spread to distant parts of the body, such as from one organ and/or tissue to another not directly connected with it. The term is also used herein to refer to a tumor that develops through the metastatic process. Thus, as used herein, the term "metastasis" refers to neoplastic cell growth (e.g., tumor cell growth) in an unregulated fashion and spread to distal tissues and organs of the body. As used herein, the phrase "inhibiting metastasis" refers to slowing and/or preventing metastasis or the spread of neoplastic cells to a site remote from the primary growth area.

As used herein, the term "invasion" refers to the spread of cancer cells to surrounding tissues. As used herein, the phrase "inhibiting invasion" refers to slowing and/or preventing the spread of cancer cells to surrounding tissues.

As used herein, the term "migration" refers to movement of cancer cells in vivo or in vitro. As used herein, the phrase "inhibiting migration" refers to slowing and/or preventing movement of cancer cells in vivo or in vitro.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

As used herein, the terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "(therapeutically) effective amount" refers to an amount of an agent (e.g., a drug) effective to treat a disease or disorder in a mammal. In the case of cancer, the therapeutically effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; reduce, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

As used herein, the term "growth inhibitory amount" refers to an amount which inhibits growth of a target cancerous cell (such as a tumor cell), either in vitro or in vivo, irrespective of the mechanism by which cell growth is inhibited. In a preferred embodiment, the growth inhibitory amount inhibits growth of the target cell in cell culture by greater than about 20%, preferably greater than about 50%, most preferably greater than about 75% (e.g., from about 75% to about 100%). Growth inhibition includes slowing or reduction of cell growth and may include complete inhibition of cell growth.

The terms "cell" and "cells" are used interchangeably herein and are intended to include either a single cell or a plurality of cells unless otherwise specified. The methods provided herein can be performed on single individual cells or a population of cells.

As used herein, the term "anti-cancer agent" refers to a substance or treatment that inhibits the function of cancer cells, inhibits their formation, and/or causes their destruction in vitro or in vivo. Examples include, but are not limited to, cytotoxic agents (e.g., 5-fluorouracil, TAXOL) and anti-signaling agents (e.g., the PI3K inhibitor LY).

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston), and antiandrogens such as flutamide, nilutamide, bicalutamide, leuprolide, and goserelin, etc.

As used herein, the term "anti-signaling agent" refers to agents that interfere with cancer cell malignancy by inhibiting specific aberrant signal transduction circuits in the cell in vitro and/or in vivo. The PI3K inhibitor LY is an example of an anti-signalling agent.

In the study described in the Examples, 29 amino acids in RhoB were mutated to their corresponding residues in RhoA to identify those residues critical to the ability of RhoB to inhibit malignant transformation. It was found that changing cysteine 192 in RhoB to the corresponding glycine in RhoA abolished the ability of RhoB to regulate transcription and to inhibit tumor proliferation, colony formation and soft agar growth as well as to induce apoptosis. In contrast, point mutations converting RhoB amino acids 29, 100, 116, 123, 129, 141, 146, 149, 152, 154, 155, 173, 181 and 191 to their corresponding amino acids in RhoA, did not affect RhoB function. Furthermore, replacing RTDD (amino acid 140 to 143) in RhoB with the corresponding KPEE of RhoA had no effect on RhoB activity. Similarly, replacing YGSQN (residues 183-187) in RhoB with the corresponding RGKKK of RhoA or AGAAA did not affect RhoB activity. A RhoA (1-180)/RhoB (181-196) chimera was as efficient as RhoB in repressing TGFβ type II receptor promoter activity and inhibiting cell proliferation as well as inducing apoptosis. Cysteine 192 is one of the two amino acids in RhoB that are posttranslationally modified with palmitic acid and this palmitoylation has previously been suggested to be critical for the localization of RhoB to the endosomes (Adamson, P. et al. *J Biol Chem*, 1992, 267:20033-20038). Consistent with this are the results described herein, which show that the C192S mutant inhibited palmitoylation and was mislocalized. In contrast to cysteine 192, it has been shown that cysteine 189, the other palmitoylation site, is not critical for the localization or function of RhoB. Furthermore, deleting the tripeptide, GCI (188-190) in RhoB, a peptide sequence which is absent in RhoA, did not affect RhoB function. Finally, moving cysteine 192 to position 190 did not alter RhoB function either. These results indicate that palmitoylated cysteine 192 but not cysteine 189 is required for RhoB function. It was also found that cysteine 193, the site of RhoB that is prenylated by either a farnesyl or a geranylgeranyl group, is also required for the ability of RhoB to suppress transcription, to inhibit proliferation and transformation and to induce apoptosis. This is consistent with previous reports that showed that mutating cysteine 193 to serine 193 or deleting the last four amino acids of RhoB, CKVL (193-196), results in loss of RhoB function (Chen, Z. et al. *J Biol Chem*, 2000, 275:17974-17978; Lebowitz, P. F. et al. *J Biol Chem*, 1997, 272:16093-16095). These results demonstrate that both (but not each alone) palmitoylated cysteine 192 and prenylated cysteine 193 must be present in RhoB for its tumor suppressive and apoptotic activities.

Previous work has demonstrated that cysteine 192 is critical for RhoB's proper cellular localization (Adamson, P. et al. *J Biol Chem*, 1992, 267:20033-20038). However, there are no reports on the importance of this amino acid for the ability of RhoB to regulate transcription, malignant transformation and apoptosis. Furthermore, there are conflicting reports on the importance of cysteine 192 on the prenylation of cysteine 193. Adamson et al. (Adamson, P. et al. *J Biol Chem*, 1992, 267:20033-20038) showed that cysteine 193, which can be either farnesylated or geranylgeranylated in wild type RhoB, becomes mainly farnesylated in a mutant RhoB when the C-terminal five amino acids CCKVL (192-196) were changed to SCKVL. One interpretation given by the authors of this study was that cysteine 192 is critical to prenylation and that the double cysteine C-C (192-193) is an important recognition site for GGTase I to transfer the geranylgeranyl group to C193. In contrast to this study, Armstrong et al. (Armstrong, S. A. et al. *J Biol Chem*, 1995, 270:7864-7868) found that cysteine 192 was not important to the prenylation of cysteine 193, and that the C192S RhoB mutant was as efficiently farnesylated or geranylgeranylated as wild type RhoB. In addition, a report from Baron et al. (Baron, R. et al. *Proc Natl Acad Sci USA*, 2000, 97:11626-11631) demonstrated that RhoB prenylation on cysteine 193 is only driven by the nature of the three carboxyl terminal KVL (194-196) residues. It is clear from the present study that a RhoB mutant that lacks palmitoylated cysteine 192, but not 189, is unable to localize properly. What is even more important is that this mutant is inactive in its ability to suppress malignant transformation and induce apoptosis even though it is still prenylated. This, coupled with the fact that the RhoA/RhoB chimera behaves like RhoB, not RhoA, leads the present inventor to conclude that one of the major reasons for the opposing effects of RhoA and RhoB on malignant transformation may reside, at least in part, in their different cellular localization from which they affect different effectors.

U.S. patent publication no. 2003/0018003 (Sebti) and U.S. patent publication no. 2004/0171547 (Sebti) describe compositions and methods using wild-type RhoB polypeptides and encoding nucleic acids encoding wild-type RhoB polypeptides, and are incorporated herein by reference in their entirety.

Materials and Methods

Site-directed Mutagenesis. Site-specific mutations were generated using the EXSITE mutagenesis kit (STRATAGENE, La Jolla, Calif.). Target genes were modified by introducing a silent mutation to provide a new restriction site in the construct without affecting the coding residue (Wang, D. A. et al. *J Biol Chem*, 2001, 276:49213-49220). For the chimera construct, bold sequences are from RhoB and the rest of the primer sequence was matched with RhoA (Table 5). All mutants were verified by complete sequencing. The corresponding primers and silent mutation of all mutants are shown in the Table 5.

TABLE 5

RhoR mutants and Primers.

| Mutants | Forward primer | Reverse primer | New restriction site |
|---|---|---|---|
| E29A | gttccccgaggtgtacgtgcccac (SEQ ID NO: 1) | gcgtccttactgaacacgatcagcag (SEQ ID NO: 2) | Mlu1 |
| V100T | ccggaggtgaagcacttctgtcccaa (SEQ ID NO: 3) | agtccacttctcggggatgttctccag (SEQ ID NO: 4) | AccIII |

TABLE 5-continued

RhoR mutants and Primers.

| Mutants | Forward primer | Reverse primer | New restriction site |
|---|---|---|---|
| A116G | agtgggtaacaaaaaagacctgcgcagcg (SEQ ID NO: 5) | agtatgatgggcacattgggacagaa (SEQ ID NO: 6) | SpeI |
| S123N | ccggacagagctggcccgcatgaa (SEQ ID NO: 7) | acatgctcgtcgttgcgcagg tctt (SEQ ID NO: 8) | AccIII |
| V127T | cgtacagagctggcccgcatgaa (SEQ ID NO: 9) | cgtatgctcgtcgctgcgcaggtctt (SEQ ID NO: 10) | MluI |
| T129R | gagagagctggcccgcatgaagcagg (SEQ ID NO: 11) | cggacatgctcgtcgctgcgcag (SEQ ID NO: 12) | AccIII |
| RTDD143KPEE | agagggccgcgccatggccgtgcgcatcc (SEQ ID NO: 13) | tctggcttcacgggttcctgcttcatgcgggc (SEQ ID NO: 14) | NcoI |
| T141P | cctgatgacggccgcgccatggccg (SEQ ID NO: 15) | cctcacgggttcctgcttcatgcgg (SEQ ID NO: 16) | StuI |
| A146D | gcgacatggccgtgcgcatccaagcct (SEQ ID NO: 17) | Gaccgtcatccgtgcgcacgggttc (SEQ ID NO: 18) | NruI |
| V149N | atccaagcctacgactacctcga (SEQ ID NO: 19) | tcgattggccatggcgcggccgtcatc (SEQ ID NO: 20) | EcoRI |
| Q152G | atgactacctcgagtgctctgccaa (SEQ ID NO: 21) | atgctccgatgcgcacggccatggcgc (SEQ ID NO: 22) | NdeI |
| Y154F | ttcgactacctcgagtgctctgccaa (SEQ ID NO: 23) | agcttggatgcgcacggccatggc (SEQ ID NO: 24) | HindIII |
| D155G | tacggctacctcgagtgctctgccaag (SEQ ID NO: 25) | agcttggatgcgcacggccatggc (SEQ ID NO: 26) | HindIII |
| T173M | cgtgccgcgctgcag aagcgctacg (SEQ ID NO: 27) | cgtgg ccatctcgaagacctcgcgcac (SEQ ID NO: 28) | Mlu1 |
| K181A | gatcccagaacggctgcatcaact (SEQ ID NO: 29) | cgtagcgcgcctgcagcgcggcgcgc (SEQ ID NO: 30) | BamHI |
| YGSQN187AGAAA | agctgccggctgcatcaactgctgcaagg (SEQ ID NO: 31) | gcgccggcgcgcttctgcagcgcggcgcgc (SEQ ID NO: 32) | PvuII |
| YGSQN187RGKKK | gcaagaaaaagggctgcatc actgctgcaaggt (SEQ ID NO: 33) | cgcggcgcttctgcagcgcggcgcgc (SEQ ID NO: 34) | SacII |
| N191S | agctgctgcaaggtgctatgagaat (SEQ ID NO: 35) | gatgcagccgttctgggagccgt (SEQ ID NO: 36) | PvuII |
| C192A | gcgtgcaaggtgctatgagaattctgc (SEQ ID NO: 37) | Gttgatgcagccgttctgggagc (SEQ ID NO: 38) | MluI |
| GCI190 | gaacaactgctgcaaggtgctatgagaat (SEQ ID NO: 39) | tgggatccgtagcgcttctgcagc (SEQ ID NO: 40) | BamHI |
| GCINCCKVL196 GCCNICKVL | atcggatccatgtacccttatg (SEQ ID NO: 41) | atagatatctcatagcaccttgcagatgttgca gcagcc (SEQ ID NO: 42) | BamHI |
| C193S | atcggatccatgtacccttatg (SEQ ID NO: 43) | Atagatatctcatagcaccttggagcagttgat (SEQ ID NO: 44) | BamHI |
| C192S | atcggatccatgtacccttatg (SEQ ID NO: 45) | atagatatctcatagcaccttgcaggagttgat (SEQ ID NO: 46) | BamHI |
| C192G | atcggatccatgtacccttatg (SEQ ID NO: 47) | atagatatctcatagcaccttgcaccggttgat (SEQ ID NO: 48) | BamHI |
| C189S, C192S | atcggatccatgtacccttatg (SEQ ID NO: 49) | atagatatctcatagcaccttgcaggagttgat ggagcc (SEQ ID NO: 50) | BamHI |
| C189S | atcggatccatgtacccttatg (SEQ ID NO: 51) | atagatatctcatagcaccttgcagcagttgat ggagcc (SEQ ID NO: 52) | BamHI |

Mutated nucleotides in RhoB are shown in bold.
Silent mutations to introduce new enzyme restriction site are shown underlined.

Cell culture and Transfection. Human pancreatic Panc-1 and prostate PC-3 cancer cells (American Type Culture Collection (ATCC) Manassas, Va.) were maintained in Dulbecco's modified minimal essential medium (DMEM) containing 10% fetal bovine serum (FBS). One day prior to transfection, $3 \times 10^5$ cells were seeded into 6-well plates. Cells were transfected with 2.5 µg of each expression construct using Cytofectene (BIO-RAD Laboratories, Hercules, Calif.) following the manufacturer's recommendation.

Metabolic Labeling. HEK293 cells (ATCC) were transfected with 5 ug plasmid DNA/100 mm dish. After transfection, cells were grown in 10% FBS/DMEM, 80 uCi/ml [$^{14}$C] palmitic acid and 5 mM sodium pyruvate for 48 hours (Adamson, P. et al. *J Biol Chem*, 1992, 267:20033-20038). Cells were washed twice with phosphate buffered saline (PBS) and lysed with 1% Triton X-100, 50 mM Tris-Cl (pH 8.0), 150 mM NaCl, 0.02% sodium azide, 100 ug/ml phenylmethylsulfonylfluoride (PMSF) and 1 µg/ml aprotinin. Lysates were collected and centrifuged for 10 min (12,000×g) at 4° C. 70 µl of supernatant of each sample was used for Western blotting. The remainder of the supernatants was incubated with anti-HA agarose conjugate (SIGMA-ALDRICH, St. Louis, Mo.) at 4° C. overnight. Pelleted beads were washed five times with lysis buffer and subjected to SDS-polyacrylamide gel electrophoresis. Gels were dried and subjected to autoradiography.

In vitro translation/prenylation. 1 ug of each DNA construct was mixed with 25 ul of Rabbit Reticulocyte lysate (Promega) and 3 uCi of $^3$H-FPP or $^3$H-GGPP at 30° C. for 90 min. For determining the protein levels produced in the in vitro translation assay, 20 uCi $^{35}$S-Methionine were used instead of $^3$H-FPP or $^3$H-GGPP. The labeled proteins were then run on SDS-polyacrylamide gels (12.5%). The gels were then dried, labeled and fluorographed with FUJI X-RAY film for 7-30 days at −80° C. (20).

Regulation of Ap1, p21waf, TGF β receptor promoter activities. Panc-1 cells were seeded at $3 \times 10^5$/well in six-well plates. 24 hours later they were transfected with 0.5 µg of p21waf, TGF β receptor II or AP1 promoter-luciferase constructs (Adnane, J. et al. *Mol Cell Biol*, 1998, 18:6962-6970; Adnane, J. et al. *J Biol Chem*, 2002, 277:8500-8507; Paradis, P. et al. *J Biol Chem*, 1996, 271:10827-10833), 0.2 µg of pCMV-β-Gal and 2 µg of each of RhoA, RhoB, mutants or pcDNA3 vector using Cytofectene as indicated by the supplier. 15 hours after transfection, the cells were replenished with fresh growth medium. For p21waf and TGF β receptor promoter activity analysis, cells were harvested 48 hours later and lysed in 200 µl of reporter lysis buffer (PROMEGA, Madison, Wis.). For AP1 activity analysis, 24 hours after transfection cells were washed once with DMEM and incubated in DMEM supplemented with 0.5% FBS during the next 16 hours, before harvesting and lysis. Aliquots of cell extracts were assayed for β-galactosidase and luciferase activities.

Colony Formation Assay. Two days post-transfection cells were trypsinized, counted, and seeded in duplicate into six-well plates. Cells were cultured for 3 weeks before being fixed and stained with Crystal Violet (SIGMA-ALDRICH) as described previously (Chen, Z. et al. *J Biol Chem*, 2000, 275:17974-17978).

Localization. $2 \times 10^5$ HEK293 cells were seeded onto coverslips in 6-well dishes. Two days post-transfection, cells were fixed with 4% paraformaldehyde, permeabilized and blocked with 0.2% Triton X-100 and 10% FBS in PBS. Transfected cells were stained with anti-HA antibody (ROCHE DIAGNOSTICS, Indianapolis, Ind.). Following three washes with PBS, the cells were incubated with a 1:250 dilution of fluorescein isothiocyanate-conjugated anti-mouse IgG secondary antibody (SIGMA-ALDRICH). Cells were visualized using a fluorescence microscope (LEICA MICROSYSTEMS, Bannockburn, Ill.), and pictures were taken with a digital camera (DIAGNOSTIC INSTRUMENTS, Sterling Heights, Mich.).

Western Blot Analysis. Two days post-transfection, cells were washed once with cold PBS and lysed in 30 mM HEPES (pH 7.5), 10 mM NaCl, 5 mM $MgCl_2$, 25 mM NaF, 1 mM EGTA, 1% Triton X-100, 10% glycerol, 2 mM sodium orthovanadate, 10 µg/ml aprotinin, 10 µg/ml soybean trypsin inhibitor, 25 µg/ml leupeptin, 2 mM PMSF, and 6.4 mg/ml p-nitrophenyl phosphate. Blots were incubated with specific antibodies as indicated in the figure legends. Antibodies were incubated in 5% milk in PBS (pH 7.4) containing 0.1% Tween 20 either 2 hours at room temperature or overnight at 4° C. Western blots were visualized using enhanced chemiluminescence.

Anchorage-independent Growth Assays. For soft agar growth assays, the transfected Panc-1 cells were seeded at 5000 cells/well in six-well plates in 0.3% agar over a 0.6% agar layer as described previously (Jiang, K. et al. *Mol Cell Biol*, 2004, 24:5565-5576). Cultures were fed once weekly until colonies grew to a suitable size (four weeks) for observation. Colonies were photographed after 3 hours incubation with 1 mg/ml MTT in the DMEM medium.

MTT Assay. Panc-1 cells were seeded on a flat-bottomed 96-well plate at $4 \times 10^3$ cells/well in 10% FBS/DMEM and transfected the next day with 0.3 µg of each construct using Cytofectene in each well. Thirty hours later, medium was replaced with fresh 10% FBS/DMEM. After 2 days of culture, medium was replaced with 1 mg/ml MTT in the DMEM medium for three hours. DMSO was added to each well before absorbance at 540 nm was read on an automated microplate reader.

In Vitro Cellular Proliferation and TUNEL Assay. Two days post-transfection, cells were harvested by trypsinization and counted via trypan blue exclusion assay to determine cellular viability. Cells (10,000-25,000) were then spun onto glass slides using a Cytospin 3 centrifuge (THERMO SHANDON, Pittsburgh, Pa.). After fixing cells to the slides with 4% paraformaldehyde in PBS (pH 7.5) for 1 hour at room temperature, cells were labeled for apoptotic DNA strand breaks by TUNEL reaction using an in situ cell death detection kit (ROCHE DIAGNOSTICS) according to the manufacturer's instructions, then mounted in Vectashield mounting medium (VECTOR LABORATORIES, Burlingame, Calif.) containing 4',6-diamidino-2-phenylindole (DAPI) to counterstain DNA. Fluorescein-labeled DNA strand breaks (TUNEL-positive cells) were then visualized using a fluorescence microscope (LEICA MICROSYSTEMS), and pictures were taken with a digital camera (DIAGNOSTIC INSTRUMENTS). TUNEL-positive nuclei were counted and compared with DAPI-stained nuclei to determine the percentage induction of apoptosis.

It should be understood that the examples and embodiments described herein are for illustrative purposes only and that various modifications or changes in light thereof will be suggested to persons skilled in the art and are to be included within the spirit and purview of this application.

EXAMPLE 1

RhoB/RhoA Site-Directed Mutagenesis Screen of 27 Mutants Identifies Cysteine 192 as a Critical Amino Acid Required for RhoB Function RhoA and RhoB share 86% amino acid sequence identity, yet RhoA promotes whereas RhoB suppresses tumorigenesis.

Figure 1C:
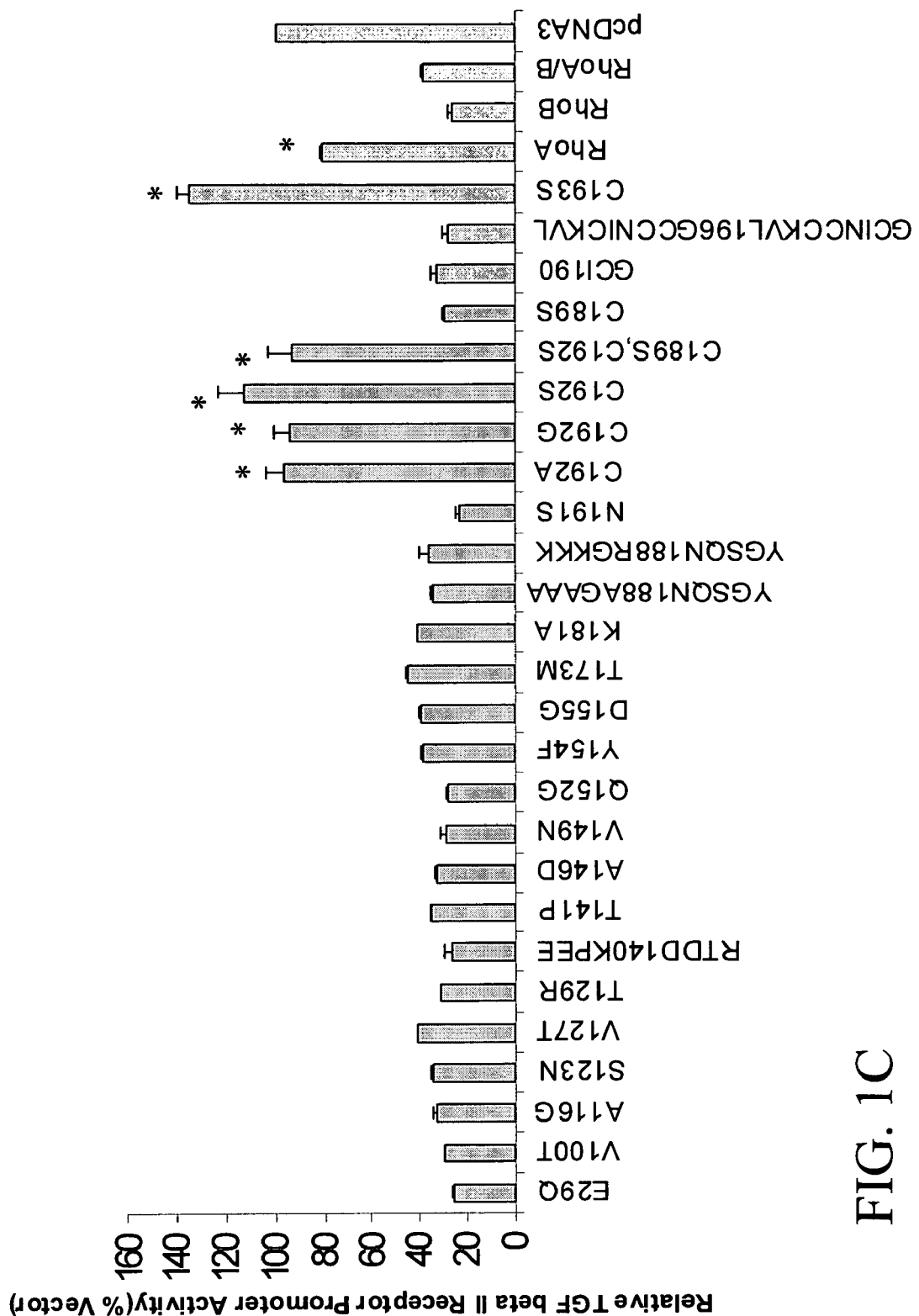

To identify amino acids in RhoB that are critical to its tumor suppressive activity, amino acids 29, 100, 116, 123, 129, 140-143, 141, 146, 152, 154, 155, 173, 181, 183-187, 189, 190, 191, 192 and 193 in RhoB were first mutagenized to the corresponding residues in RhoA (FIG. 1A and Table 5). A RhoA (1-180)/RhoB (181-196) chimera was also made (Table 5). The resulting 26 mutant proteins as well as wild type RhoB and RhoA were expressed in Panc-1 cells, and their effects on TGFβ type II receptor (TGFβ II R) promoter transcriptional activity were determined. TGFβ II R promoter/luciferase reporter was used as an initial screen for RhoB function as it had been shown previously that RhoB suppresses TGFβ II R promoter activity (Adnane, J. et al. *J Biol Chem*, 2002, 277:8500-8507). FIG. 1B shows that all HA-tagged RhoB mutants as well as wild type HA-RhoB and wild type HA-RhoA were expressed in Panc-1 cells, whereas as expected pcDNA3 vector-transfected cells were devoid of HA-tagged proteins. FIG. 1C shows that ectopic expression of wild type RhoB but not RhoA resulted in inhibition of TGFβ II R promoter transcriptional activity. Out of the 27 mutant proteins generated, only those in which cysteine 192 or cysteine 193 were mutated lost their ability to suppress TGFβ II R promoter transcriptional activity (FIG. 1C). Cysteine 193, the amino acid that is prenylated (both farnesylated and geranylgeranylated), has previously been shown to be important for RhoB function, whereas cysteine 192, one of the two palmitoylation sites (189 and 192) in RhoB, has not previously been implicated in RhoB function. Furthermore, whereas cysteine 192 was critical for inhibiting TGFβ II R transcriptional activity, cysteine 189, the other palmitoylated site, was not. Mutating both cysteines 189 and 192 to serines also abolished the ability of RhoB to inhibit TGFβ II R promoter activity. Mutating cysteine 192 to either glycine (the corresponding residue in RhoA), alanine or serine all resulted in loss of RhoB's ability to inhibit TGFβ II R promoter activity (FIG. 1C). In contrast, point mutations converting RhoB amino acids 29, 100, 116, 123, 129, 141, 146, 149, 152, 154, 155, 173, 181 and 191 to their corresponding amino acids in RhoA, did not affect the ability of RhoB to inhibit TGFβ II R promoter activity. The RhoA/RhoB chimera behaved like RhoB, not RhoA (FIG. 1C). Furthermore, replacing RTDD (amino acid 140 to 143) in RhoB by their corresponding KPEE in RhoA had no effect on RhoB activity (FIG. 1C). Similarly, replacing YGSQN (residues 183-187) in RhoB by their corresponding RGKKK in RhoA or AGAAA did not affect RhoB activity. Moving palmitoylated cysteine 192 to position 190 also did not affect RhoB activity. Finally, deleting the tripeptide GCI, residues 188-190 in RhoB, which is absent in RhoA, did not affect RhoB's ability to inhibit TGFβ II R promoter activity (FIG. 1C).

EXAMPLE 2

Figure 1D:
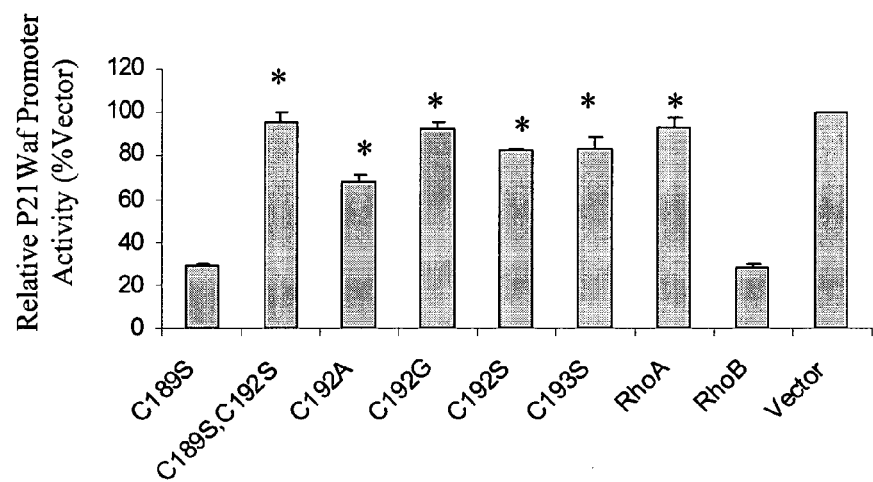
Figure 1E:
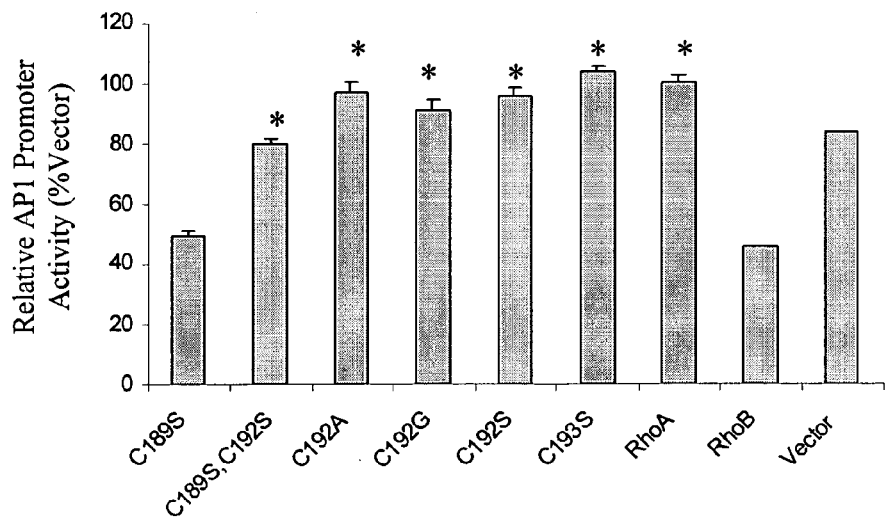

Cysteine 192 is Required for RhoB Inhibition of p21waf and AP-1 Promoter Transcriptional Activities The results described above clearly demonstrate that presence of cysteine 192 or cysteine 193 alone is insufficient and that they must both be present in RhoB in order for this protein to suppress TGFβ II R promoter transcriptional activity. To further confirm the importance of these two amino acids in RhoB function, the effects of the corresponding mutant proteins on p21 waf and AP-1 promoter activities were evaluated. FIGS. 1D and 1E show that ectopic expression of either wild type RhoB or C189S RhoB mutant resulted in inhibition of p21waf and AP-1 promoter activities. In contrast, RhoA and RhoB point mutants C193S, C192S, C192A, C192G and double mutant C189S/C192S were unable to inhibit p21waf and AP-1 promoter activity.

EXAMPLE 3

C 192 S and C 193 S Mutations Inhibit Palmitoylation and Mislocalize RhoB

Figure 2A:
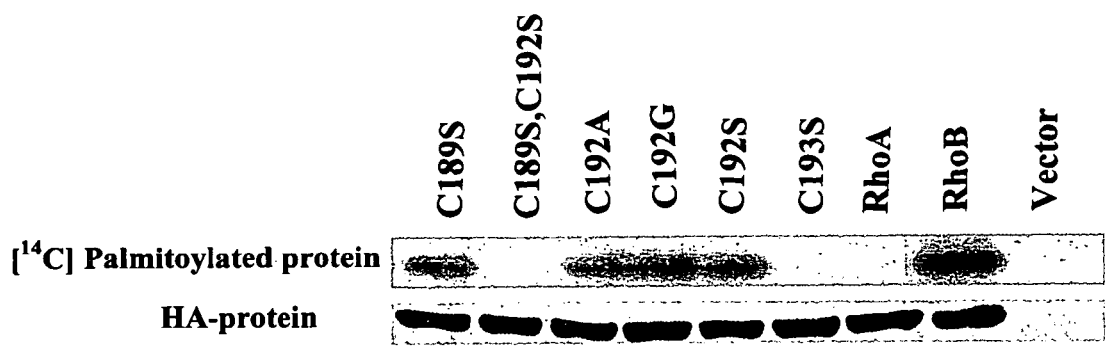
FIGS. 2A-2C show palmitoylation and localization of RhoA, RhoB and mutants.
Figure 2C:
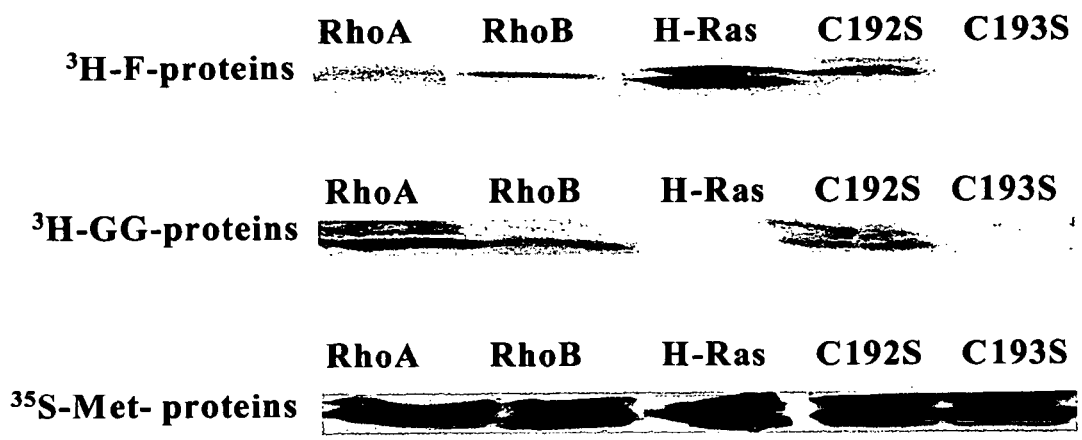
Figure 2B:
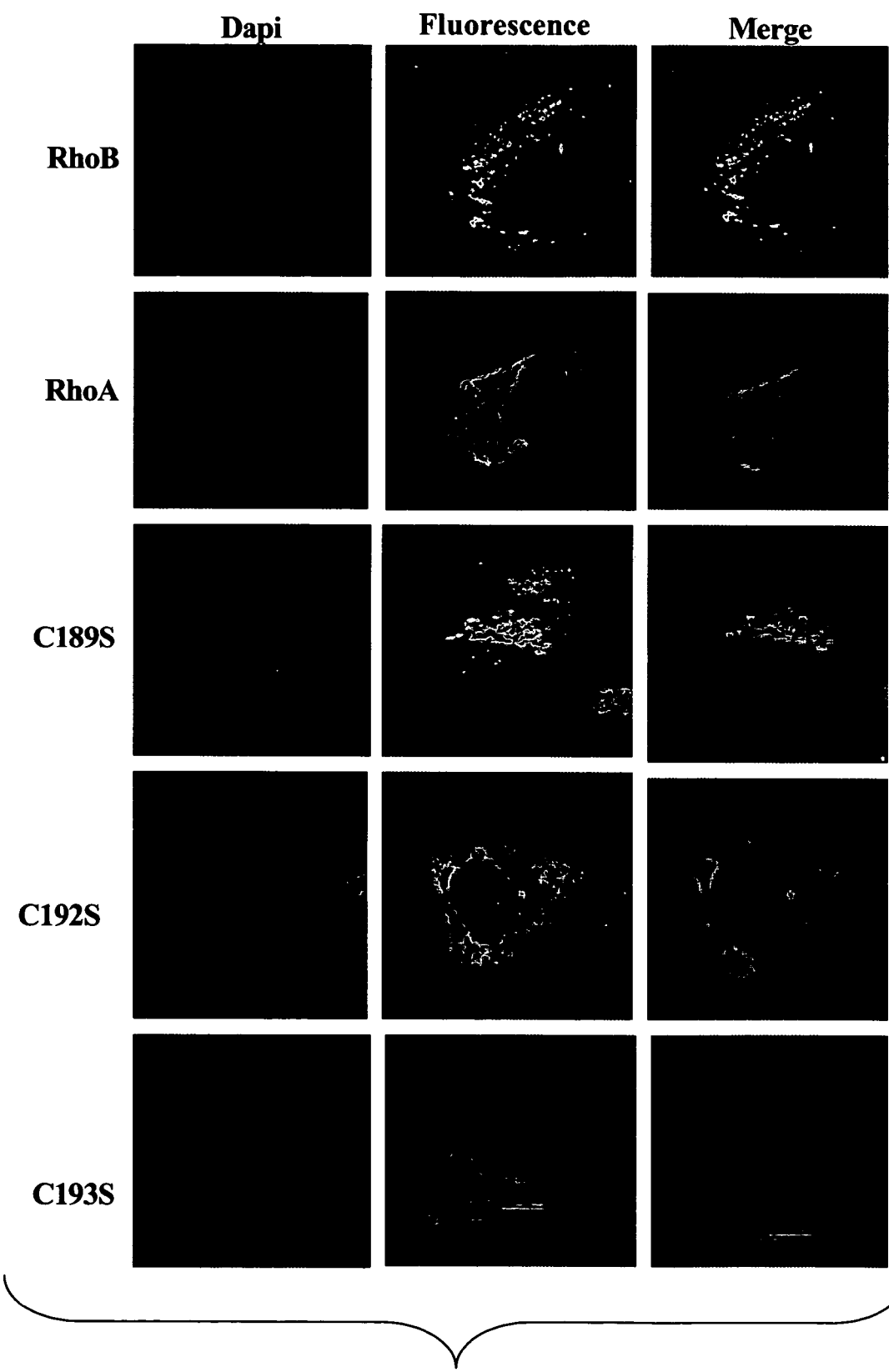

Next, the effect of cysteines 189, 192 and 193 on palmitoylation and cellular localization of RhoB were determined. As expected, mutating both cysteines 189 and 192 to serines resulted in a RhoB protein devoid of [$^{14}$C] palmitic acid label (FIG. 2A). Furthermore, mutating one of these two cysteines at a time resulted in half the [$^{14}$C] palmitic acid labeling as wild type RhoB which contains both cysteines. Mutating cysteine 193 to serine prevented palmitoylation suggesting that prenylation of cysteine 193 is required for palmitoylation of cysteines 189 and 192 to occur. Finally, as expected, RhoA, which is known to lack palmitoylation sites, was not found to contain any [$^{14}$C] palmitic acid label (FIG. 2A). Next, the effects of the mutations on the cellular localization of RhoB were determined. FIG. 2B shows that wild type RhoB showed a punctate profile consistent with the previously reported endosome localization (Adamson, P. et al. *J Biol Chem*, 1992, 267:20033-20038), whereas RhoA showed a diffused profile and was predominantly cytosolic. Furthermore, C192S and C193S RhoB mutants localized to the cytosol whereas the C 189S mutant showed a punctate profile similar to that of wild type RhoB (FIG. 2B).

EXAMPLE 4

C 192 S Mutation does not Affect Prenylation of RhoB

There are conflicting reports on the importance of cysteine 192 on the prenylation status of cysteine 193. While Adamson et al. (Adamson, P. et al. *J Biol Chem*, 1992, 267:20033-20038) reported that cysteine 192 RhoB mutant becomes mainly farnesylated, Armstrong et al (Armstrong, S. A. et al. *J Biol Chem*, 1995, 270:7864-7868) found that cysteine 192 mutant was both farnesylated and geranylgeranylated. Using in vitro translation/prenylation assays, it was demonstrated that C192S RhoB mutant was farnesylated and geranylgeranylated as efficiently as wild type RhoB (FIG. 2C).

EXAMPLE 5

Figure 3A:
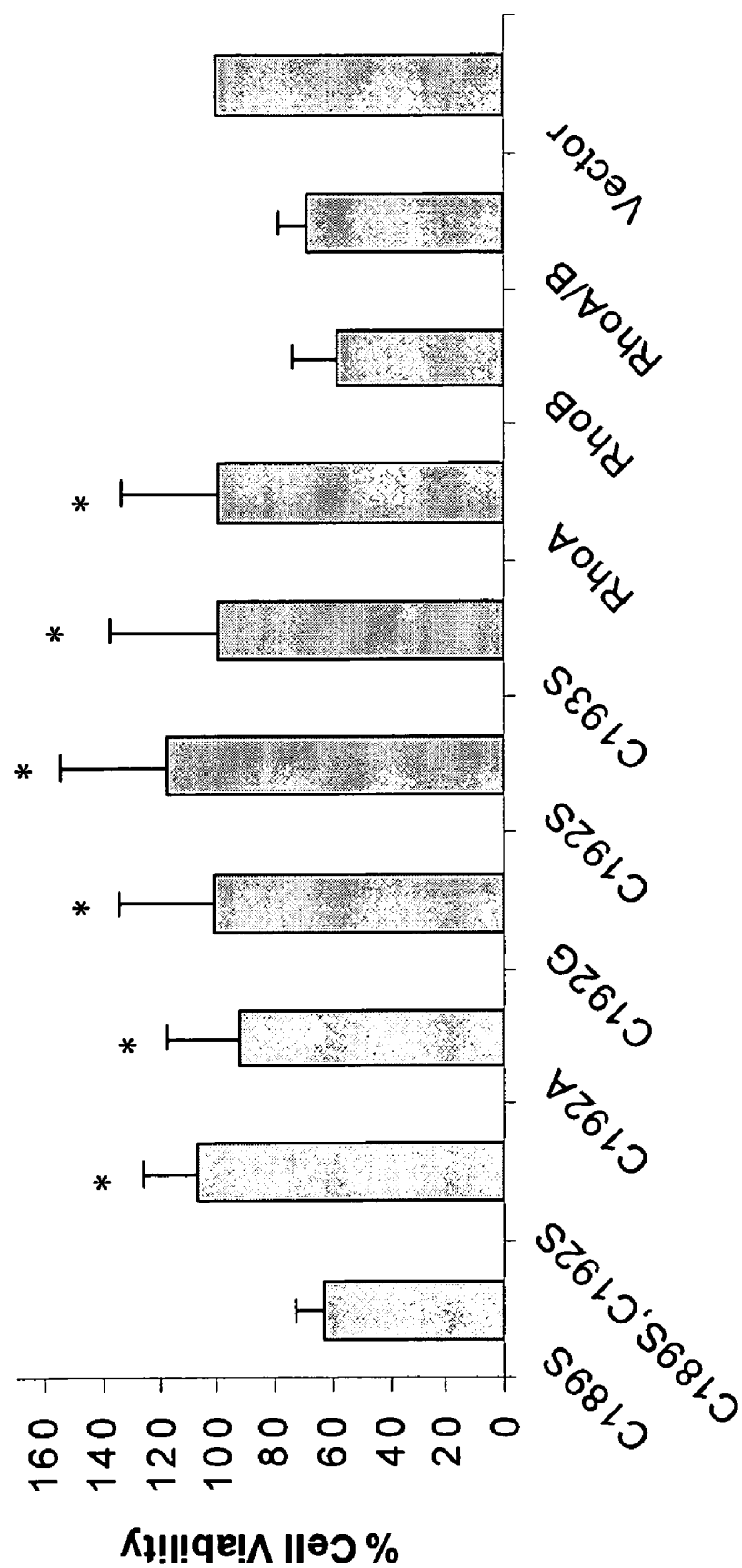
FIGS. 3A-3C show that cysteine 192 and cysteine 193 but not cysteine 189 are required for RhoB to suppress tumor cell growth.
Figure 3B:
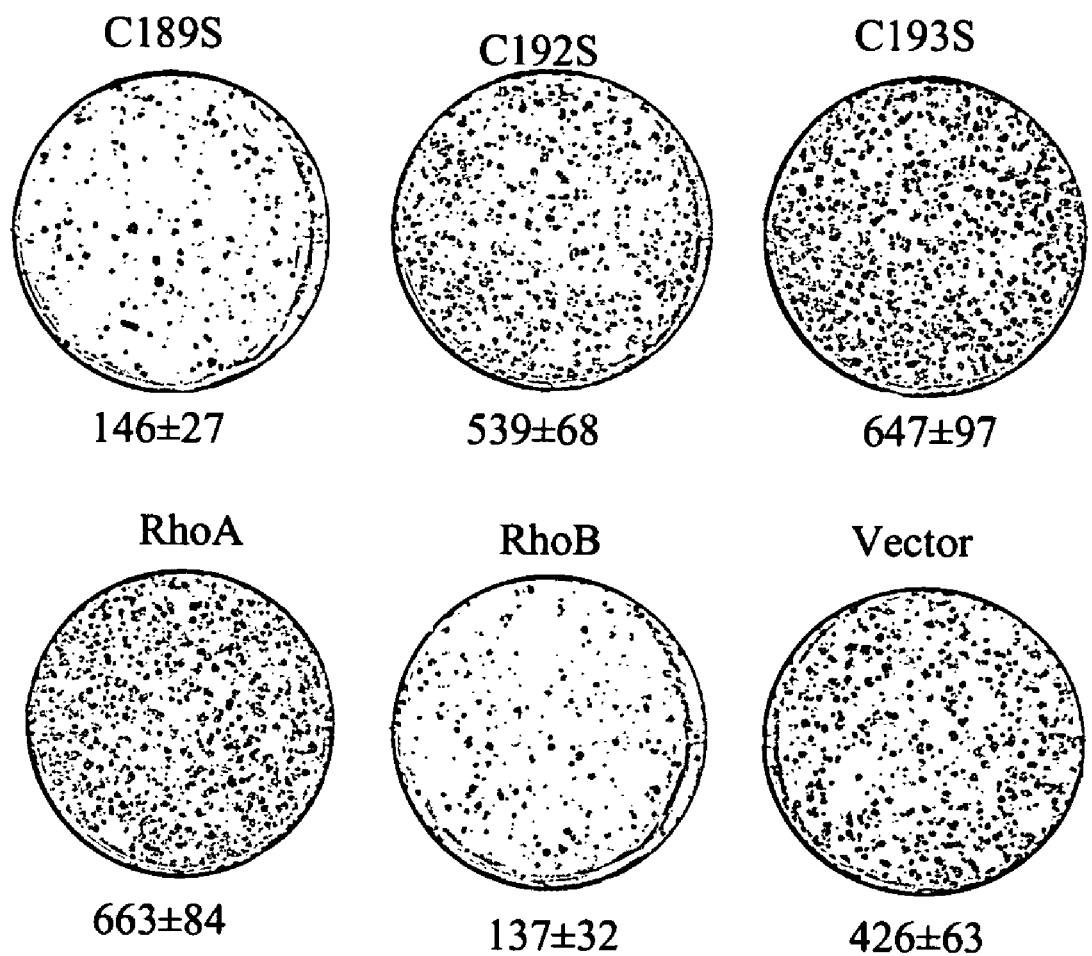
Figure 3C:
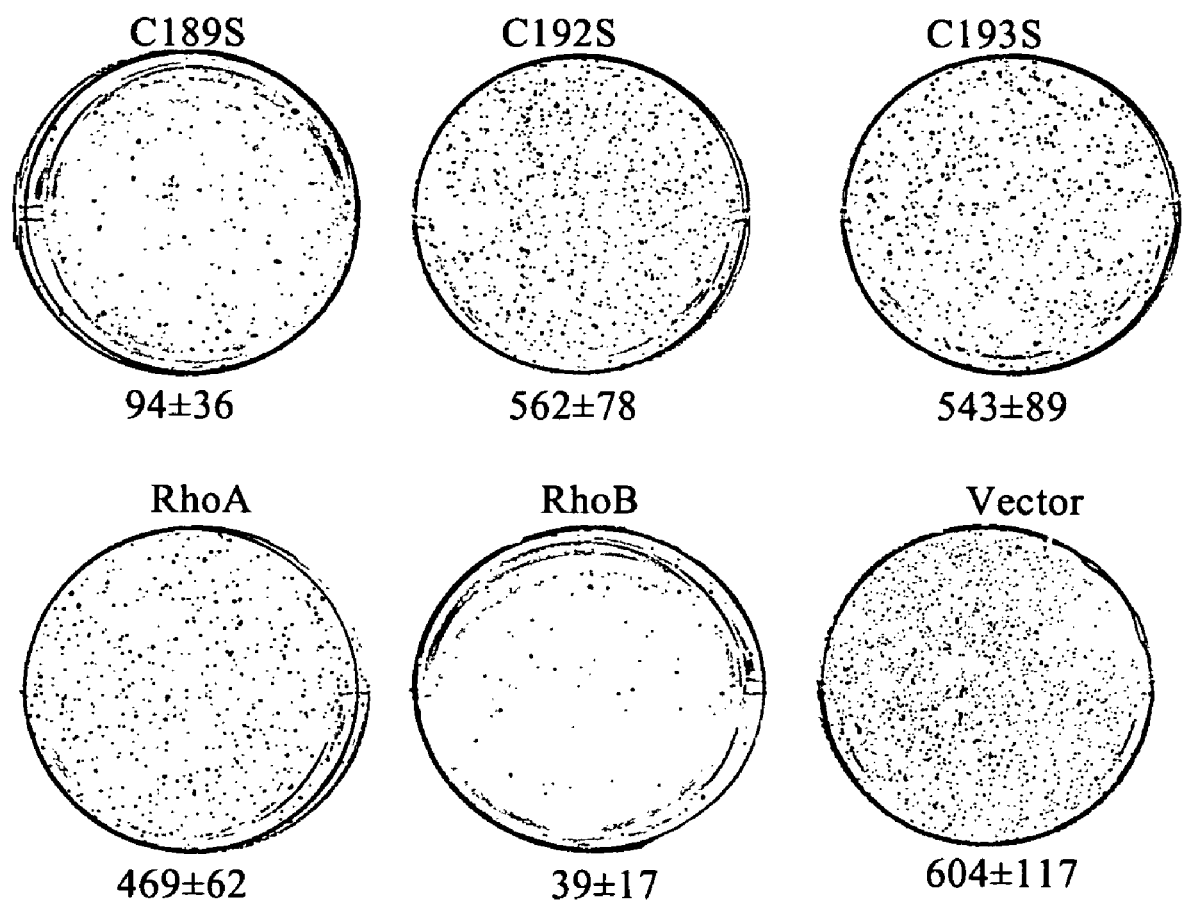

Palmitoylated Cysteine 192 is Required for RhoB to Inhibit Anchorage-Dependent and -Independent Tumor Growth FIGS. 1 and 2 demonstrated that point mutations at one palmitoylation site (cysteine 192) but not the other (cysteine 189) resulted in a RhoB protein mutant that was mislocalized and that was unable to carry out its signaling function that led to downregulation of the transcriptional activities of TGFβ II R, AP-1 and p21waf promoters. Next, the effects of the point mutations on RhoB tumor suppressive activity were determined. FIG. 3A shows that ectopic expression of wild type RhoB, as well as the RhoA/B chimera, but not RhoA, inhibited proliferation (anchorage-dependent tumor growth) of PC3 tumor cells by 40%. In contrast, ectopic expression of point mutants C193S, C192S, C192A, C 192G, but not C189S, abolished the ability of RhoB to inhibit PC3 tumor cell proliferation. Next, the effects of the mutations on the ability of RhoB to inhibit Panc-1 tumor cell colony formation on plastic were determined. FIG. 3B shows that wild type RhoB (137±32 colonies) and point mutant C189S (146±27 colonies) inhibited Panc-1 colony formation compared to vector control (426±23). In contrast, RhoA (663±84 colonies) as well as RhoB point mutants C192S (538±68 colonies) and C193S (647±97 colonies) increased Panc-1 colony formation. Similarly, FIG. 3C shows that wild type RhoB (39±17) and RhoB point mutant C189S (94±36 colonies) but not RhoA (469±62 colonies) and RhoB point mutants C192S (562±78 colonies) and C193S (543±89 colonies) inhibited relative to vector control (684±117 colonies) soft agar colony formation (anchorage-independent tumor growth).

EXAMPLE 6

Figure 4A:
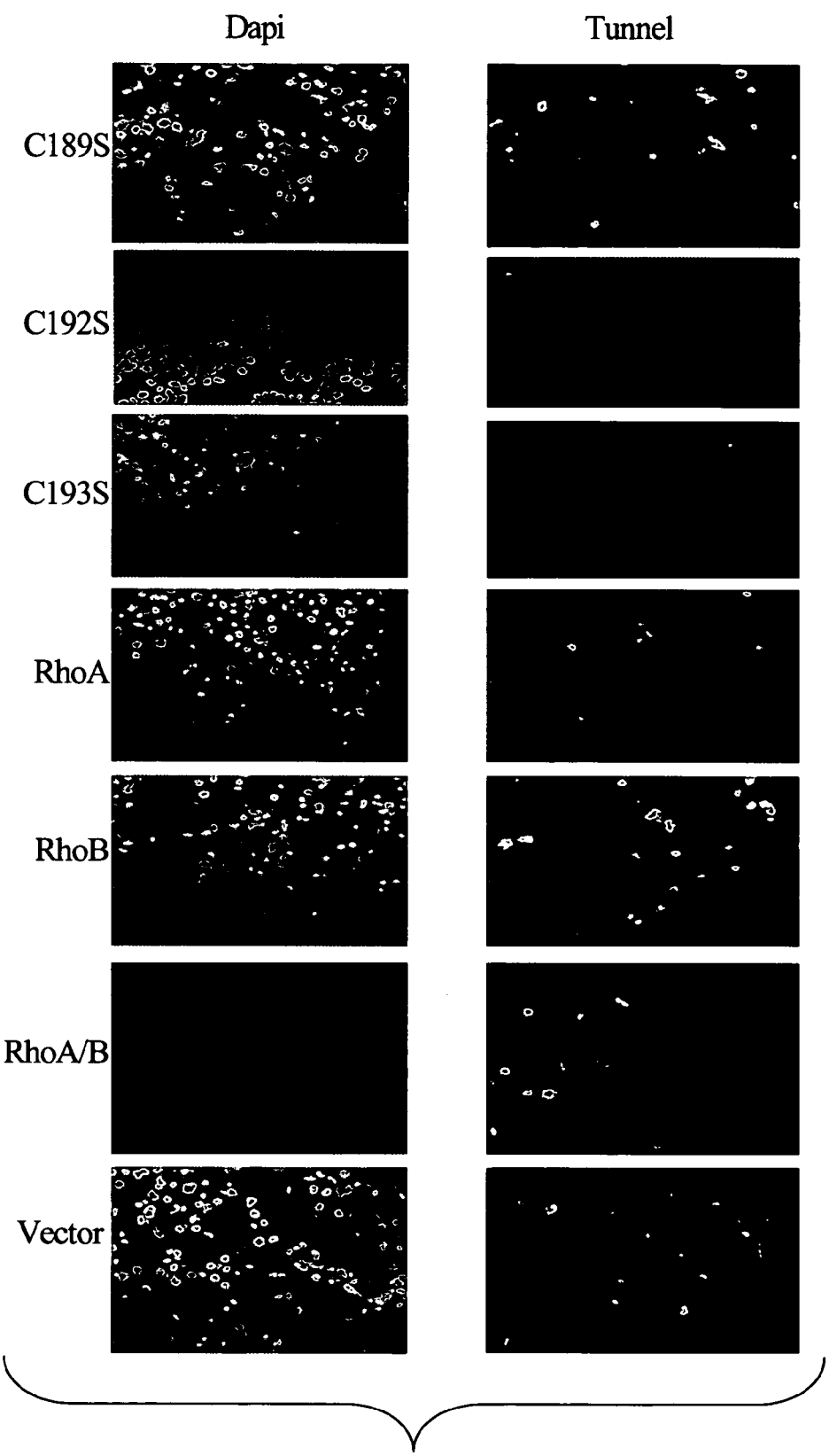
FIGS. 4A-4B show that cysteine 192 and cysteine 193 mutations block the ability of RhoB to induce apoptosis.
Figure 4B:
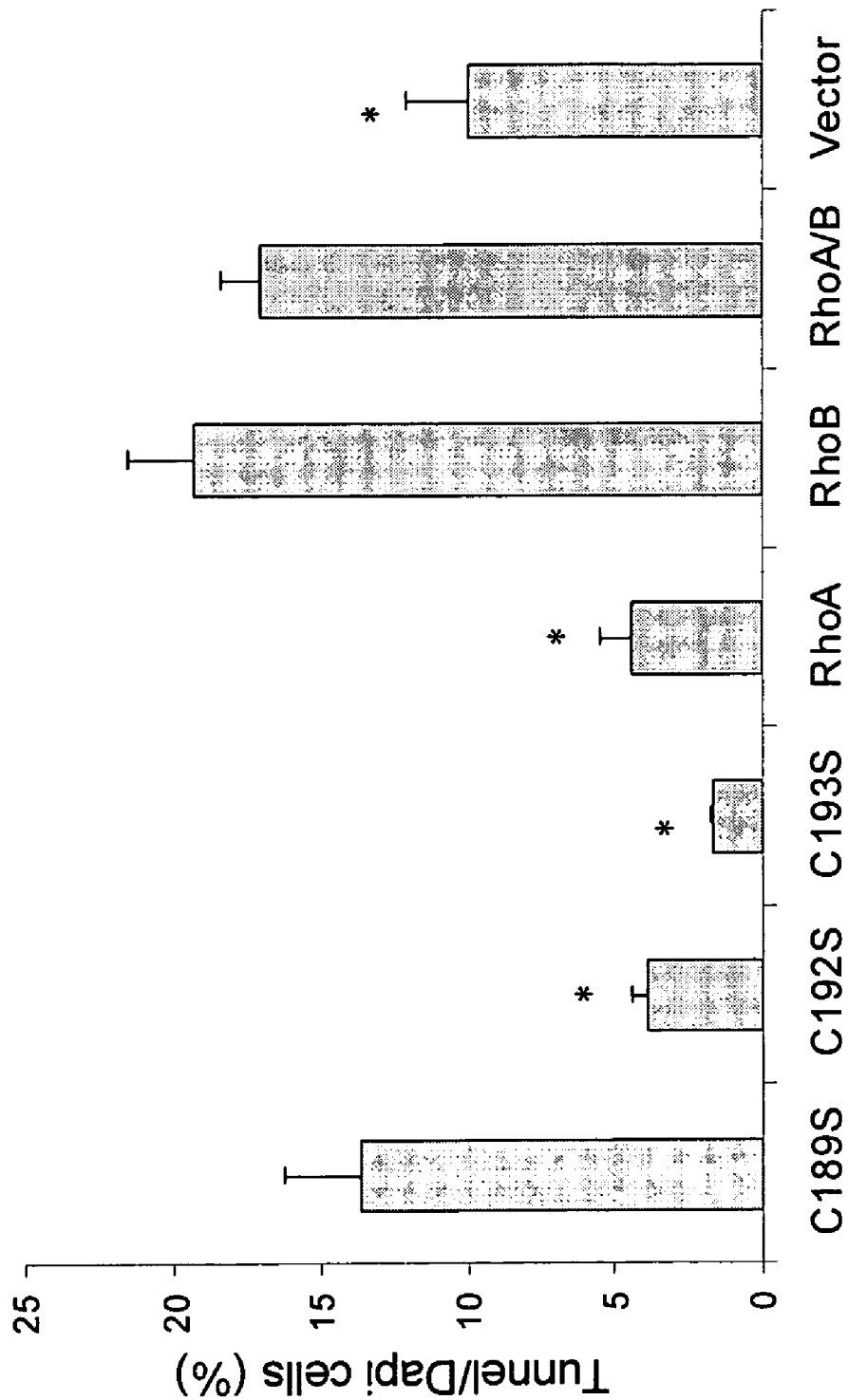

Palmitoylated Cysteine 192, but not Palmitoylated Cysteine 189 is Required for RhoB to Induce Apoptosis FIG. 3 results above show that the palmitoylated site of one cysteine (192) but not the other (189) along with the prenylation site cysteine 193 are critical for RhoB tumor cell growth. Because RhoB is also known to induce programmed cell death (apoptosis), the importance of cysteines 192 and 193 on the ability of RhoB to induce apoptosis by Tunel staining was determined next. FIGS. 4A and 4B show that vector transfected cells contained 10±2% apoptotic cells, whereas cells transfected with RhoB, C189S RhoB, or the RhoA/B chimera mutant contained 19±2%, 14±2%, and 17±1% apoptotic cells, respectively. In contrast, cells transfected with RhoA and point mutants C193S or C192S contained only 4±1%, 2±0.4%, or 4±0.5% apoptotic cells, respectively. Therefore, C192S and C193S mutations blocked the ability of RhoB to induce apoptosis.

All patents, patent applications, provisional applications, and publications referred to or cited herein are incorporated by reference in their entirety, including all figures and tables, to the extent they are not inconsistent with the explicit teachings of this specification.

I claim:

1. An isolated polynucleotide comprising a nucleic acid sequence encoding a human RhoB variant polypeptide comprising an amino acid sequence having at least one point mutation relative to the human wild-type RhoB polypeptide, wherein the human wild-type RhoB polypetide comprises the amino acid sequence of SEQ ID NO:54, and wherein said human RhoB variant polypeptide exhibits inhibition of TGF-βII receptor promoter transcriptional activity characteristic of human wild-type RhoB polypeptide, and wherein said at least one point mutation is at an amino acid position in the human wild-type RhoB polypeptide selected from the group consisting of 29, 100, 116, 123, 127, 129, 143, 141, 146, 149, 152, 154, 155, 173, 181, 187, 190, and 191.

2. A vector comprising a nucleic acid sequence encoding a human RhoB variant polypeptide comprising an amino acid sequence having at least one point mutation relative to the human wild-type RhoB polypeptide, wherein the human wild-type RhoB polypeptide comprises the amino acid sequence of SEQ ID NO:54, and wherein said human RhoB variant polypeptide exhibits inhibition of TGF-β II receptor promoter transcriptional activity characteristic of human wild-type RhoB polypeptide, and wherein said at least one point mutation is at an amino acid position in the human wild-type RhoB polypeptide selected from the group consisting of 29, 100, 116, 123, 127, 129, 143, 141, 146, 149, 152, 154, 155, 173, 181, 187, 190, and 191.

3. An isolated host cell genetically modified to express a nucleic acid sequence encoding a human RhoB variant polypeptide comprising an amino acid sequence having at least one point mutation relative to the human wild-type RhoB polypeptide, wherein the human wild-type RhoB polypeptide comprises the amino acid sequence of SEQ ID NO:54, and wherein said human RhoB variant polypeptide exhibits inhibition of TGF-βII receptor promoter transcriptional activity characteristic of human wild-type RhoB polypeptide, and wherein said at least one point mutation occurs is at an amino acid position in the human wild-type RhoB polypeptide selected from the group consisting of 29, 100, 116, 123, 127, 129, 143, 141, 146, 149, 152, 154, 155, 173, 181, 187, 190, and 191.

4. A composition comprising a polynucleotide encoding human RhoB variant polypeptide comprising an amino acid sequence having at least one point mutation relative to the human wild-type RhoB polypeptide, wherein the human wild-type RhoB polypeptide comprises the amino acid sequence of SEQ ID NO:54, and wherein said human RhoB variant polypeptide exhibits inhibition of TGF-β II receptor promoter transcriptional activity characteristic of human wild-type RhoB polypeptide; and a pharmaceutically acceptable carrier, and wherein said at least one point mutation occurs is at an amino acid position in the human wild-type RhoB polypeptide selected from the group consisting of 29, 100, 116, 123, 127, 129, 143, 141, 146, 149, 152, 154, 155, 173, 181, 187, 190, and 191.

5. The isolated polynucleotide of claim 1, wherein said human RhoB variant polypeptide comprises the N191S mutation and at least one point mutation selected from the group consisting of E29A, V100T, A116G, S123N, V127T, T129R, RTDD143KPEE (SEQ ID NO:57), T141P, A146D, V149N, Q152G, Y154F, D155G, T173M, K181A, YGSQN187AGAAA (SEQ ID NO:55), YGSQN187RGKKK (SEQ ID NO:56), 1190C, or a conservative amino acid substitution of one or more of the foregoing.

6. The vector of 9, wherein said human RhoB variant polypeptide comprises the N191S mutation and at least one point mutation selected from the group consisting of E29A, V100T, A116G, S123N, V127T, T129R, RTDD143KPEE (SEQ ID NO:57), T141P, A146D, V149N, Q152G, Y154F, D155G, T173M, K181A, YGSQN187AGAAA (SEQ ID NO:55), YGSQN187RGKKK (SEQ ID NO:56), 1190C, or a conservative amino acid substitution of one or more of the foregoing.

7. The isolated host cell of claim 3, wherein said human RhoB variant polypeptide comprises the N191S mutation and at least one point mutation selected from the group consisting of E29A, V100T, A116G, S123N, V127T, T129R, RTDD143KPEE (SEQ ID NO:57), T141P, A146D, V149N, Q152G, Y154F, D155G, T173M, K181A, YGSQN187AGAAA (SEQ ID NO:55), YGSQN187RGKKK (SEQ ID NO:56), I190C, or a conservative amino acid substitution of one or more of the foregoing.

8. The composition of claim 4, wherein said human RhoB variant polypeptide comprises the N191S mutation and at least one point mutation selected from the group consisting of E29A, V100T, A116G, S123N, V127T, T129R, RTDD143KPEE (SEQ ID NO:57), T141P, A146D, V149N, Q152G, Y154F, D155G, T173M, K181A, YGSQN187AGAAA (SEQ ID NO:55), YGSQN187RGKKK (SEQ ID NO:56), I190C, or a conservative amino acid substitution of one or more of the foregoing.

9. The polynucleotide of claim 1, wherein said at least one point mutation is at amino acid position 191 in the human wild-type RhoB polypeptide and the asparagine at position 191 in the human wild-type RhoB polypeptide is replaced by a glycine, threonine, serine, tyrosine, or glutamine.

10. The vector of claim 2, wherein said at least one point mutation is at amino acid position 191 in the human wild-type RhoB polypeptide and the asparagine at position 191 in the human wild-type RhoB polypeptide is replaced by a glycine, threonine, serine, tyrosine, or glutamine.

11. The isolated host cell of claim 3, wherein said at least one point mutation is at amino acid position 191 in the human wild-type RhoB polypeptide and the asparagine at position 191 in the human wild-type RhoB polypeptide is replaced by a glycine, threonine, serine, tyrosine, or glutamine.

12. The composition of claim 4, wherein said at least one point mutation is at amino acid position 191 in the human wild-type RhoB polypeptide and the asparagine at position 191 in the human wild-type RhoB polypeptide is replaced by a glycine, threonine, serine, tyrosine, or glutamine.

13. The polynucleotide of claim 9, wherein the asparagine at amino acid position 191 is replaced by a serine.

14. The vector of claim 10, wherein the asparagine at amino acid position 191 is replaced by a serine.

15. The isolated host cell of claim 11, wherein the asparagine at amino acid position 191 is replaced by a serine.

16. The composition of claim 12, wherein the asparagine at amino acid position 191 is replaced by a serine.

17. The isolated host cell of claim 3, wherein said host cell is a prokaryotic cell.

18. The isolated host cell of claim 17, wherein said prokaryotic cell is *E. coli*.

19. The isolated host cell of claim 3, wherein said host cell is a eukaryotic cell.

20. The vector of claim 2, wherein said vector comprises one or more of promoter sequences, terminator sequences, polyadenylation sequences, enhancer sequences, or marker gene sequences.

21. The isolated polynucleotide of claim 1, wherein said human RhoB variant polypeptide comprises the N191S mutation and at least one point mutation selected from the group consisting of E29A, V100T, A116G, V127T, T129R, RTDD143KPEE (SEQ ID NO:57), T141P, A146D, V149N, Q152G, Y154F, D155G, T173M, K181A, YGSQN187AGAAA (SEQ ID NO:55), YGSQN187RGKKK (SEQ ID NO:56), I190C, or a conservative amino acid substitution of one or more of the foregoing.

22. The vector of 2, wherein said human RhoB variant polypeptide comprises the N191S mutation and at least one point mutation selected from the group consisting of E29A, V100T, A116G, V127T, T129R, RTDD143KPEE (SEQ ID NO:57), T141P, A146D, V149N, Q152G, Y154F, D155G, T173M, K181A, YGSQN187AGAAA (SEQ ID NO:55), YGSQN187RGKIKK (SEQ ID NO:56), I190C, or a conservative amino acid substitution of one or more of the foregoing.

23. The isolated host cell of claim 3, wherein said human RhoB variant polypeptide comprises the N191S mutation and at least one point mutation selected from the group consisting of E29A, V100T, A116G, V127T, T129R, RTDD143KPEE (SEQ ID NO:57), T141P, A146D, V149N, Q152G, Y154F, D155G, T173M, K181A, YGSQN187AGAAA (SEQ ID NO:55), YGSQN187RGKKK (SEQ ID NO:56), I190C, or a conservative amino acid substitution of one or more of the foregoing.

24. The composition of claim 4, wherein said human RhoB variant polypeptide comprises the N191S mutation and at least one point mutation selected from the group consisting of E29A, V100T, A116G, V127T, T129R, RTDD143KPEE (SEQ ID NO:57), T141P, A146D, V149N, Q152G, Y154F, D155G, T173M, K181A, YGSQN187AGAAA (SEQ ID NO:55), YGSQN187RGKKK (SEQ ID NO:56), I190C, or a conservative amino acid substitution of one or more of the foregoing.

* * * * *

UNITED STATES PATENT AND TRADEMARK OFFICE
CERTIFICATE OF CORRECTION

PATENT NO. : 7,951,924 B2
APPLICATION NO. : 11/274368
DATED : May 31, 2011
INVENTOR(S) : Said M. Sebti It is certified that error appears in the above-identified patent and that said Letters Patent is hereby corrected as shown below:

Column 7,
Line 49, "acid, omithine, norleucine" should read --acid, ornithine, norleucine--.

Column 18,
Line 28, "Hroxyurea" should read --Hydroxyurea--.

Column 28,
Forward primer column corresponding to V100T, "ccggaggt..." should read --ccggaggt...--.

Column 29,
Forward primer column corresponding to RTDD143KPEE, "agagggccgcgccatgg..." should read --agagggccgcgccatgg...--.
Reverse primer column corresponding to GCI190, "tgggatccgtagcgcttctgcagc" should read --tgggatccgtagcgcttctgcagc--.
Forward primer column corresponding to C189S, "atcggatcca..." should read --atcggatcca...--.

Column 34,
Line 65, "C 192G, but not" should read --C192G, but not--.

Column 58,
Line 49, "1190C, or a" should read --I190C, or a--.
Line 58, "1190C, or a" should read --I190C, or a--.

Column 59,
Line 1, "1190C, or a" should read --I190C, or a--.

Column 60,
Line 8, "N191S" should read --N191S--.
Line 23, "YGSQN187RGKIKK" should read --YGSQN187RGKKK--.

Signed and Sealed this
Fourteenth Day of February, 2012

David J. Kappos
*Director of the United States Patent and Trademark Office*

```
                        SEQUENCE LISTING

<160> NUMBER OF SEQ ID NOS: 57

<210> SEQ ID NO 1
<211> LENGTH: 24
<212> TYPE: DNA
<213> ORGANISM: Artificial Sequence
<220> FEATURE:
<223> OTHER INFORMATION: Forward primer

<400> SEQUENCE: 1
gttccccgag gtgtacgtgc ccac                                              24

<210> SEQ ID NO 2
<211> LENGTH: 26
<212> TYPE: DNA
<213> ORGANISM: Artificial Sequence
<220> FEATURE:
<223> OTHER INFORMATION: Reverse primer

<400> SEQUENCE: 2
gcgtccttac tgaacacgat cagcag                                            26

<210> SEQ ID NO 3
<211> LENGTH: 26
<212> TYPE: DNA
<213> ORGANISM: Artificial Sequence
<220> FEATURE:
<223> OTHER INFORMATION: Forward primer

<400> SEQUENCE: 3
ccggaggtga agcacttctg tcccaa                                            26

<210> SEQ ID NO 4
<211> LENGTH: 27
<212> TYPE: DNA
<213> ORGANISM: Artificial Sequence
<220> FEATURE:
<223> OTHER INFORMATION: Reverse primer

<400> SEQUENCE: 4
agtccacttc tcggggatgt tctccag                                           27
```

```
<210> SEQ ID NO 5
<211> LENGTH: 29
<212> TYPE: DNA
<213> ORGANISM: Artificial Sequence
<220> FEATURE:
<223> OTHER INFORMATION: Forward primer

<400> SEQUENCE: 5
agtgggtaac aaaaaagacc tgcgcagcg                                          29

<210> SEQ ID NO 6
<211> LENGTH: 26
<212> TYPE: DNA
<213> ORGANISM: Artificial Sequence
<220> FEATURE:
<223> OTHER INFORMATION: Reverse primer

<400> SEQUENCE: 6
agtatgatgg gcacattggg acagaa                                             26

<210> SEQ ID NO 7
<211> LENGTH: 24
<212> TYPE: DNA
<213> ORGANISM: Artificial Sequence
<220> FEATURE:
<223> OTHER INFORMATION: Forward primer

<400> SEQUENCE: 7
ccggacagag ctggcccgca tgaa                                               24

<210> SEQ ID NO 8
<211> LENGTH: 25
<212> TYPE: DNA
<213> ORGANISM: Artificial Sequence
<220> FEATURE:
<223> OTHER INFORMATION: Reverse primer

<400> SEQUENCE: 8
acatgctcgt cgttgcgcag gtctt                                              25

<210> SEQ ID NO 9
<211> LENGTH: 23
<212> TYPE: DNA
<213> ORGANISM: Artificial Sequence
<220> FEATURE:
<223> OTHER INFORMATION: Forward primer

<400> SEQUENCE: 9
cgtacagagc tggcccgcat gaa                                                23

<210> SEQ ID NO 10
<211> LENGTH: 26
<212> TYPE: DNA
<213> ORGANISM: Artificial Sequence
<220> FEATURE:
<223> OTHER INFORMATION: Reverse primer

<400> SEQUENCE: 10
cgtatgctcg tcgctgcgca ggtctt                                             26

<210> SEQ ID NO 11
<211> LENGTH: 26
<212> TYPE: DNA
<213> ORGANISM: Artificial Sequence
<220> FEATURE:
<223> OTHER INFORMATION: Forward primer

<400> SEQUENCE: 11
```

-continued

```
gagagagctg gcccgcatga agcagg                                      26

<210> SEQ ID NO 12
<211> LENGTH: 23
<212> TYPE: DNA
<213> ORGANISM: Artificial Sequence
<220> FEATURE:
<223> OTHER INFORMATION: Reverse primer

<400> SEQUENCE: 12
cggacatgct cgtcgctgcg cag                                         23

<210> SEQ ID NO 13
<211> LENGTH: 29
<212> TYPE: DNA
<213> ORGANISM: Artificial Sequence
<220> FEATURE:
<223> OTHER INFORMATION: Forward primer

<400> SEQUENCE: 13
agagggccgc gccatggccg tgcgcatcc                                   29

<210> SEQ ID NO 14
<211> LENGTH: 32
<212> TYPE: DNA
<213> ORGANISM: Artificial Sequence
<220> FEATURE:
<223> OTHER INFORMATION: Reverse primer

<400> SEQUENCE: 14
tctggcttca cgggttcctg cttcatgcgg gc                               32

<210> SEQ ID NO 15
<211> LENGTH: 25
<212> TYPE: DNA
<213> ORGANISM: Artificial Sequence
<220> FEATURE:
<223> OTHER INFORMATION: Forward primer

<400> SEQUENCE: 15
cctgatgacg gccgcgccat ggccg                                       25

<210> SEQ ID NO 16
<211> LENGTH: 25
<212> TYPE: DNA
<213> ORGANISM: Artificial Sequence
<220> FEATURE:
<223> OTHER INFORMATION: Reverse primer

<400> SEQUENCE: 16
cctcacgggt tcctgcttca tgcgg                                       25

<210> SEQ ID NO 17
<211> LENGTH: 27
<212> TYPE: DNA
<213> ORGANISM: Artificial Sequence
<220> FEATURE:
<223> OTHER INFORMATION: Forward primer

<400> SEQUENCE: 17
gcgacatggc cgtgcgcatc caagcct                                     27

<210> SEQ ID NO 18
<211> LENGTH: 25
<212> TYPE: DNA
<213> ORGANISM: Artificial Sequence
```

```
<220> FEATURE:
<223> OTHER INFORMATION: Reverse primer

<400> SEQUENCE: 18
gaccgtcatc cgtgcgcacg ggttc                                    25

<210> SEQ ID NO 19
<211> LENGTH: 23
<212> TYPE: DNA
<213> ORGANISM: Artificial Sequence
<220> FEATURE:
<223> OTHER INFORMATION: Forward primer

<400> SEQUENCE: 19
atccaagcct acgactacct cga                                      23

<210> SEQ ID NO 20
<211> LENGTH: 27
<212> TYPE: DNA
<213> ORGANISM: Artificial Sequence
<220> FEATURE:
<223> OTHER INFORMATION: Reverse primer

<400> SEQUENCE: 20
tcgattggcc atggcgcggc cgtcatc                                  27

<210> SEQ ID NO 21
<211> LENGTH: 25
<212> TYPE: DNA
<213> ORGANISM: Artificial Sequence
<220> FEATURE:
<223> OTHER INFORMATION: Forward primer

<400> SEQUENCE: 21
atgactacct cgagtgctct gccaa                                    25

<210> SEQ ID NO 22
<211> LENGTH: 27
<212> TYPE: DNA
<213> ORGANISM: Artificial Sequence
<220> FEATURE:
<223> OTHER INFORMATION: Reverse primer

<400> SEQUENCE: 22
atgctccgat gcgcacggcc atggcgc                                  27

<210> SEQ ID NO 23
<211> LENGTH: 26
<212> TYPE: DNA
<213> ORGANISM: Artificial Sequence
<220> FEATURE:
<223> OTHER INFORMATION: Forward primer

<400> SEQUENCE: 23
ttcgactacc tcgagtgctc tgccaa                                   26

<210> SEQ ID NO 24
<211> LENGTH: 24
<212> TYPE: DNA
<213> ORGANISM: Artificial Sequence
<220> FEATURE:
<223> OTHER INFORMATION: Reverse primer

<400> SEQUENCE: 24
agcttggatg cgcacggcca tggc                                     24
```

```
<210> SEQ ID NO 25
<211> LENGTH: 27
<212> TYPE: DNA
<213> ORGANISM: Artificial Sequence
<220> FEATURE:
<223> OTHER INFORMATION: Forward primer

<400> SEQUENCE: 25
tacggctacc tcgagtgctc tgccaag                                       27

<210> SEQ ID NO 26
<211> LENGTH: 24
<212> TYPE: DNA
<213> ORGANISM: Artificial Sequence
<220> FEATURE:
<223> OTHER INFORMATION: Reverse primer

<400> SEQUENCE: 26
agcttggatg cgcacggcca tggc                                          24

<210> SEQ ID NO 27
<211> LENGTH: 25
<212> TYPE: DNA
<213> ORGANISM: Artificial Sequence
<220> FEATURE:
<223> OTHER INFORMATION: Forward primer

<400> SEQUENCE: 27
cgtgccgcgc tgcagaagcg ctacg                                         25

<210> SEQ ID NO 28
<211> LENGTH: 27
<212> TYPE: DNA
<213> ORGANISM: Artificial Sequence
<220> FEATURE:
<223> OTHER INFORMATION: Reverse primer

<400> SEQUENCE: 28
cgtggccatc tcgaagacct cgcgcac                                       27

<210> SEQ ID NO 29
<211> LENGTH: 24
<212> TYPE: DNA
<213> ORGANISM: Artificial Sequence
<220> FEATURE:
<223> OTHER INFORMATION: Forward primer

<400> SEQUENCE: 29
gatcccagaa cggctgcatc aact                                          24

<210> SEQ ID NO 30
<211> LENGTH: 26
<212> TYPE: DNA
<213> ORGANISM: Artificial Sequence
<220> FEATURE:
<223> OTHER INFORMATION: Reverse primer

<400> SEQUENCE: 30
cgtagcgcgc ctgcagcgcg gcgcgc                                        26

<210> SEQ ID NO 31
<211> LENGTH: 29
<212> TYPE: DNA
<213> ORGANISM: Artificial Sequence
<220> FEATURE:
<223> OTHER INFORMATION: Forward primer

<400> SEQUENCE: 31
```
agctgccggc tgcatcaact gctgcaagg          29

<210> SEQ ID NO 32
<211> LENGTH: 30
<212> TYPE: DNA
<213> ORGANISM: Artificial Sequence
<220> FEATURE:
<223> OTHER INFORMATION: Reverse primer

<400> SEQUENCE: 32
gcgccggcgc gcttctgcag cgcggcgcgc          30

<210> SEQ ID NO 33
<211> LENGTH: 33
<212> TYPE: DNA
<213> ORGANISM: Artificial Sequence
<220> FEATURE:
<223> OTHER INFORMATION: Forward primer

<400> SEQUENCE: 33
gcaagaaaaa gggctgcatc actgctgcaa ggt          33

<210> SEQ ID NO 34
<211> LENGTH: 26
<212> TYPE: DNA
<213> ORGANISM: Artificial Sequence
<220> FEATURE:
<223> OTHER INFORMATION: Reverse primer

<400> SEQUENCE: 34
cgcggcgctt ctgcagcgcg gcgcgc          26

<210> SEQ ID NO 35
<211> LENGTH: 25
<212> TYPE: DNA
<213> ORGANISM: Artificial Sequence
<220> FEATURE:
<223> OTHER INFORMATION: Forward primer

<400> SEQUENCE: 35
agctgctgca aggtgctatg agaat          25

<210> SEQ ID NO 36
<211> LENGTH: 23
<212> TYPE: DNA
<213> ORGANISM: Artificial Sequence
<220> FEATURE:
<223> OTHER INFORMATION: Reverse primer

<400> SEQUENCE: 36
gatgcagccg ttctgggagc cgt          23

<210> SEQ ID NO 37
<211> LENGTH: 27
<212> TYPE: DNA
<213> ORGANISM: Artificial Sequence
<220> FEATURE:
<223> OTHER INFORMATION: Forward primer

<400> SEQUENCE: 37
gcgtgcaagg tgctatgaga attctgc          27

<210> SEQ ID NO 38
<211> LENGTH: 23
<212> TYPE: DNA
<213> ORGANISM: Artificial Sequence -continued

```
<220> FEATURE:
<223> OTHER INFORMATION: Reverse primer

<400> SEQUENCE: 38
gttgatgcag ccgttctggg agc                                          23

<210> SEQ ID NO 39
<211> LENGTH: 29
<212> TYPE: DNA
<213> ORGANISM: Artificial Sequence
<220> FEATURE:
<223> OTHER INFORMATION: Forward primer

<400> SEQUENCE: 39
gaacaactgc tgcaaggtgc tatgagaat                                    29

<210> SEQ ID NO 40
<211> LENGTH: 24
<212> TYPE: DNA
<213> ORGANISM: Artificial Sequence
<220> FEATURE:
<223> OTHER INFORMATION: Reverse primer

<400> SEQUENCE: 40
tgggatccgt agcgcttctg cagc                                         24

<210> SEQ ID NO 41
<211> LENGTH: 22
<212> TYPE: DNA
<213> ORGANISM: Artificial Sequence
<220> FEATURE:
<223> OTHER INFORMATION: Forward primer

<400> SEQUENCE: 41
atcggatcca tgtaccctta tg                                           22

<210> SEQ ID NO 42
<211> LENGTH: 39
<212> TYPE: DNA
<213> ORGANISM: Artificial Sequence
<220> FEATURE:
<223> OTHER INFORMATION: Reverse primer

<400> SEQUENCE: 42
atagatatct catagcacct tgcagatgtt gcagcagcc                         39

<210> SEQ ID NO 43
<211> LENGTH: 22
<212> TYPE: DNA
<213> ORGANISM: Artificial Sequence
<220> FEATURE:
<223> OTHER INFORMATION: Forward primer

<400> SEQUENCE: 43
atcggatcca tgtaccctta tg                                           22

<210> SEQ ID NO 44
<211> LENGTH: 33
<212> TYPE: DNA
<213> ORGANISM: Artificial Sequence
<220> FEATURE:
<223> OTHER INFORMATION: Reverse primer

<400> SEQUENCE: 44
atagatatct catagcacct tggagcagtt gat                               33
```

```
<210> SEQ ID NO 45
<211> LENGTH: 22
<212> TYPE: DNA
<213> ORGANISM: Artificial Sequence
<220> FEATURE:
<223> OTHER INFORMATION: Forward primer

<400> SEQUENCE: 45
atcggatcca tgtacccttp tg                                              22

<210> SEQ ID NO 46
<211> LENGTH: 33
<212> TYPE: DNA
<213> ORGANISM: Artificial Sequence
<220> FEATURE:
<223> OTHER INFORMATION: Reverse primer

<400> SEQUENCE: 46
atagatatct catagcacct tgcaggagtt gat                                  33

<210> SEQ ID NO 47
<211> LENGTH: 22
<212> TYPE: DNA
<213> ORGANISM: Artificial Sequence
<220> FEATURE:
<223> OTHER INFORMATION: Forward primer

<400> SEQUENCE: 47
atcggatcca tgtacccttp tg                                              22

<210> SEQ ID NO 48
<211> LENGTH: 33
<212> TYPE: DNA
<213> ORGANISM: Artificial Sequence
<220> FEATURE:
<223> OTHER INFORMATION: Reverse primer

<400> SEQUENCE: 48
atagatatct catagcacct tgcaccggtt gat                                  33

<210> SEQ ID NO 49
<211> LENGTH: 22
<212> TYPE: DNA
<213> ORGANISM: Artificial Sequence
<220> FEATURE:
<223> OTHER INFORMATION: Forward primer

<400> SEQUENCE: 49
atcggatcca tgtacccttp tg                                              22

<210> SEQ ID NO 50
<211> LENGTH: 39
<212> TYPE: DNA
<213> ORGANISM: Artificial Sequence
<220> FEATURE:
<223> OTHER INFORMATION: Reverse primer

<400> SEQUENCE: 50
atagatatct catagcacct tgcaggagtt gatggagcc                            39

<210> SEQ ID NO 51
<211> LENGTH: 22
<212> TYPE: DNA
<213> ORGANISM: Artificial Sequence
<220> FEATURE:
<223> OTHER INFORMATION: Forward primer

<400> SEQUENCE: 51
```

```
atcggatcca tgtacccttta tg                                              22
```

<210> SEQ ID NO 52
<211> LENGTH: 39
<212> TYPE: DNA
<213> ORGANISM: Artificial Sequence
<220> FEATURE:
<223> OTHER INFORMATION: Reverse primer

<400> SEQUENCE: 52

```
atagatatct catagcacct tgcagcagtt gatggagcc                             39
```

<210> SEQ ID NO 53
<211> LENGTH: 193
<212> TYPE: PRT
<213> ORGANISM: Homo sapiens
<220> FEATURE:
<221> NAME/KEY: MISC_FEATURE
<222> LOCATION: (1)..(193)
<223> OTHER INFORMATION: RhoA amino acid sequence (partial)

<400> SEQUENCE: 53

```
Met Ala Ala Ile Arg Lys Lys Leu Val Ile Val Gly Asp Gly Ala Cys
 1               5                  10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu
```

<210> SEQ ID NO 54
<211> LENGTH: 196
<212> TYPE: PRT
<213> ORGANISM: Homo sapiens
<220> FEATURE:
<221> NAME/KEY: MISC_FEATURE
<222> LOCATION: (1)..(196)
<223> OTHER INFORMATION: RhoB amino acid sequence (partial)

<400> SEQUENCE: 54

```
Met Ala Ala Ile Arg Lys Lys Leu Val Val Val Gly Asp Gly Ala Cys
 1               5                  10                  15
```

```
Gly Lys Thr Cys Leu Leu Ile Val Phe Ser Lys Asp Glu Phe Pro Glu
            20                  25                  30

Val Tyr Val Pro Thr Val Phe Glu Asn Tyr Val Ala Asp Ile Glu Val
            35                  40                  45

Asp Gly Lys Gln Val Glu Leu Ala Leu Trp Asp Thr Ala Gly Gln Glu
 50                  55                  60

Asp Tyr Asp Arg Leu Arg Pro Leu Ser Tyr Pro Asp Thr Asp Val Ile
 65                  70                  75                  80

Leu Met Cys Phe Ser Val Asp Ser Pro Asp Ser Leu Glu Asn Ile Pro
                85                  90                  95

Glu Lys Trp Val Pro Glu Val Lys His Phe Cys Pro Asn Val Pro Ile
            100                 105                 110

Ile Leu Val Ala Asn Lys Lys Asp Leu Arg Ser Asp Glu His Val Arg
            115                 120                 125

Thr Glu Leu Ala Arg Met Lys Gln Glu Pro Val Arg Thr Asp Asp Gly
            130                 135                 140

Arg Ala Met Ala Val Arg Ile Gln Ala Tyr Asp Tyr Leu Glu Cys Ser
145                 150                 155                 160

Ala Lys Thr Lys Glu Gly Val Arg Glu Val Phe Glu Thr Ala Thr Arg
            165                 170                 175

Ala Ala Leu Gln Lys Arg Tyr Gly Ser Gln Asn Gly Cys Ile Asn Cys
            180                 185                 190

Cys Lys Val Leu
            195

<210> SEQ ID NO 55
<211> LENGTH: 196
<212> TYPE: PRT
<213> ORGANISM: Homo sapiens
<220> FEATURE:
<221> NAME/KEY: MISC_FEATURE
<222> LOCATION: (1)..(196)
<223> OTHER INFORMATION: RhoB amino acid sequence (partial)

<400> SEQUENCE: 55

Met Ala Ala Ile Arg Lys Lys Leu Val Val Gly Asp Gly Ala Cys
1               5                   10                  15

Gly Lys Thr Cys Leu Leu Ile Val Phe Ser Lys Asp Glu Phe Pro Glu
            20                  25                  30

Val Tyr Val Pro Thr Val Phe Glu Asn Tyr Val Ala Asp Ile Glu Val
            35                  40                  45

Asp Gly Lys Gln Val Glu Leu Ala Leu Trp Asp Thr Ala Gly Gln Glu
 50                  55                  60

Asp Tyr Asp Arg Leu Arg Pro Leu Ser Tyr Pro Asp Thr Asp Val Ile
 65                  70                  75                  80

Leu Met Cys Phe Ser Val Asp Ser Pro Asp Ser Leu Glu Asn Ile Pro
                85                  90                  95

Glu Lys Trp Val Pro Glu Val Lys His Phe Cys Pro Asn Val Pro Ile
            100                 105                 110

Ile Leu Val Ala Asn Lys Lys Asp Leu Arg Ser Asp Glu His Val Arg
            115                 120                 125

Thr Glu Leu Ala Arg Met Lys Gln Glu Pro Val Arg Thr Asp Asp Gly
            130                 135                 140

Arg Ala Met Ala Val Arg Ile Gln Ala Tyr Asp Tyr Leu Glu Cys Ser
145                 150                 155                 160

Ala Lys Thr Lys Glu Gly Val Arg Glu Val Phe Glu Thr Ala Thr Arg
            165                 170                 175
```

```
Ala Ala Leu Gln Lys Arg Ala Gly Ala Ala Gly Cys Ile Ser Cys
            180                 185                 190

Cys Lys Val Leu
        195

<210> SEQ ID NO 56
<211> LENGTH: 196
<212> TYPE: PRT
<213> ORGANISM: Homo sapiens
<220> FEATURE:
<221> NAME/KEY: MISC_FEATURE
<222> LOCATION: (1)..(196)
<223> OTHER INFORMATION: RhoB amino acid sequence (partial)

<400> SEQUENCE: 56

Met Ala Ala Ile Arg Lys Lys Leu Val Val Val Gly Asp Gly Ala Cys
1               5                   10                  15

Gly Lys Thr Cys Leu Leu Ile Val Phe Ser Lys Asp Glu Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Val Asp Ser Pro Asp Ser Leu Glu Asn Ile Pro
                85                  90                  95

Glu Lys Trp Val Pro Glu Val Lys His Phe Cys Pro Asn Val Pro Ile
            100                 105                 110

Ile Leu Val Ala Asn Lys Lys Asp Leu Arg Ser Asp Glu His Val Arg
        115                 120                 125

Thr Glu Leu Ala Arg Met Lys Gln Glu Pro Val Arg Thr Asp Asp Gly
    130                 135                 140

Arg Ala Met Ala Val Arg Ile Gln Ala Tyr Asp Tyr Leu Glu Cys Ser
145                 150                 155                 160

Ala Lys Thr Lys Glu Gly Val Arg Glu Val Phe Glu Thr Ala Thr Arg
                165                 170                 175

Ala Ala Leu Gln Lys Arg Arg Gly Lys Lys Gly Cys Ile Ser Cys
            180                 185                 190

Cys Lys Val Leu
        195

<210> SEQ ID NO 57
<211> LENGTH: 196
<212> TYPE: PRT
<213> ORGANISM: Homo sapiens
<220> FEATURE:
<221> NAME/KEY: MISC_FEATURE
<222> LOCATION: (1)..(196)
<223> OTHER INFORMATION: RhoB amino acid sequence (partial)

<400> SEQUENCE: 57

Met Ala Ala Ile Arg Lys Lys Leu Val Val Val Gly Asp Gly Ala Cys
1               5                   10                  15

Gly Lys Thr Cys Leu Leu Ile Val Phe Ser Lys Asp Glu Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
```

-continued

```
    50                  55                  60

Asp Tyr Asp Arg Leu Arg Pro Leu Ser Tyr Pro Asp Thr Asp Val Ile
65                  70                  75                  80

Leu Met Cys Phe Ser Val Asp Ser Pro Asp Ser Leu Glu Asn Ile Pro
                85                  90                  95

Glu Lys Trp Val Pro Glu Val Lys His Phe Cys Pro Asn Val Pro Ile
            100                 105                 110

Ile Leu Val Ala Asn Lys Lys Asp Leu Arg Ser Asp Glu His Val Arg
        115                 120                 125

Thr Glu Leu Ala Arg Met Lys Gln Glu Pro Val Lys Pro Glu Glu Gly
    130                 135                 140

Arg Ala Met Ala Val Arg Ile Gln Ala Tyr Asp Tyr Leu Glu Cys Ser
145                 150                 155                 160

Ala Lys Thr Lys Glu Gly Val Arg Glu Val Phe Glu Thr Ala Thr Arg
                165                 170                 175

Ala Ala Leu Gln Lys Arg Tyr Gly Ser Gln Asn Gly Cys Ile Ser Cys
            180                 185                 190

Cys Lys Val Leu
        195
```